US011109916B2

(12) United States Patent
Rappel et al.

(10) Patent No.: US 11,109,916 B2
(45) Date of Patent: Sep. 7, 2021

(54) PERSONALIZED HAND-EYE COORDINATED DIGITAL STEREO MICROSCOPIC SYSTEMS AND METHODS

(71) Applicant: DIGITAL SURGICALS PTE LTD, Singapore (SG)

(72) Inventors: James Kolenchery Rappel, Singapore (SG); Amitabha Lahiri, Singapore (SG); Jose Kolenchery, Austin, TX (US)

(73) Assignee: DIGITAL SURGICALS PTE LTD, Singapore (SG)

(*) Notice: Subject to any disclaimer, the term of this patent is extended or adjusted under 35 U.S.C. 154(b) by 0 days.

(21) Appl. No.: 15/774,682

(22) PCT Filed: Nov. 9, 2016

(86) PCT No.: PCT/US2016/061056
§ 371 (c)(1),
(2) Date: May 9, 2018

(87) PCT Pub. No.: WO2017/083331
PCT Pub. Date: May 18, 2017

(65) Prior Publication Data
US 2018/0344413 A1    Dec. 6, 2018

Related U.S. Application Data

(60) Provisional application No. 62/252,704, filed on Nov. 9, 2015.

(51) Int. Cl.
*A61B 34/00* (2016.01)
*G06T 19/00* (2011.01)
(Continued)

(52) U.S. Cl.
CPC .............. *A61B 34/25* (2016.02); *A61B 34/00* (2016.02); *A61B 90/20* (2016.02); *A61B 90/361* (2016.02);
(Continued)

(58) Field of Classification Search
USPC .................................. 386/223–224, 239–248
See application file for complete search history.

(56) References Cited

U.S. PATENT DOCUMENTS

2007/0097495 A1* 5/2007 Knoblich ............... G02B 21/26
359/384
2009/0135475 A1* 5/2009 Luber .................. G02B 21/025
359/380

(Continued)

OTHER PUBLICATIONS

Feb. 27, 2017, International Search Report issued for International Application No. PCT/US2016/061056.

*Primary Examiner* — Hung Q Dang
(74) *Attorney, Agent, or Firm* — Clements Bernard Walker; Lawrence A. Baratta, Jr.; Jacob P. Beers

(57) ABSTRACT

A personalized digital microscope system for use in microsurgery includes a camera system configured to produce a stereo pair of images captured in real-time; an image processing system communicatively coupled to the camera system and configured to extract the stereo pair of images synchronized in time with each other and to combine the stereo pair of images with encoded images of differences between the stereo pair of images; and a video processing system communicatively coupled to the image processing system and configured to create a stream from the encoded images by processing the encoded images based on personalization for the user, wherein the personalization is determined based on a test procedure performed by the user.

13 Claims, 16 Drawing Sheets

(51) Int. Cl.
*A61B 90/20* (2016.01)
*A61B 90/00* (2016.01)
*H04N 13/128* (2018.01)
*H04N 13/246* (2018.01)
*H04N 13/161* (2018.01)
*H04N 13/243* (2018.01)
*G02B 21/00* (2006.01)
*G02B 21/36* (2006.01)

(52) U.S. Cl.
CPC ....... *G02B 21/0012* (2013.01); *G02B 21/365* (2013.01); *G06T 19/00* (2013.01); *H04N 13/128* (2018.05); *H04N 13/161* (2018.05); *H04N 13/243* (2018.05); *H04N 13/246* (2018.05); *A61B 2034/258* (2016.02); *A61B 2090/371* (2016.02); *A61B 2090/372* (2016.02); *A61B 2090/373* (2016.02); *G02B 21/368* (2013.01)

(56) References Cited

U.S. PATENT DOCUMENTS

| | | | |
|---|---|---|---|
| 2012/0050492 A1* | 3/2012 | Moriwake | G03B 35/08 348/47 |
| 2013/0076863 A1 | 3/2013 | Rappel | |
| 2014/0085452 A1 | 3/2014 | Nistico et al. | |
| 2015/0141755 A1* | 5/2015 | Tesar | G02B 21/368 600/111 |
| 2015/0163475 A1* | 6/2015 | Krisman | H04N 13/128 348/54 |

* cited by examiner

PERSONALIZED HAND-EYE COORDINATED DIGITAL STEREO MICROSCOPIC SYSTEMS AND METHODS

CROSS-REFERENCE TO RELATED APPLICATION(S)

The present non-provisional patent/application claims priority to U.S. Provisional Patent Application No. 62/252,704, filed Nov. 9, 2015, and entitled "PERSONALIZED HAND-EYE COORDINATED DIGITAL STEREO MICROSCOPIC SYSTEMS AND METHODS," the contents of which is incorporated by reference herein.

FIELD OF THE DISCLOSURE

The present disclosure relates generally to microscope systems and methods for surgery. More particularly, the present disclosure relates to personalized hand-eye coordinated digital stereo microscope systems and methods.

BACKGROUND OF THE DISCLOSURE

Accurate perception of depth and excellent hand-eye coordination is needed in performing dexterous tasks, such as performing anastomosis in small vessels. Surgical stereo microscopes provide both depth perception through stereopsis and hand-eye coordination, but the ergonomics of using the surgical stereo microscopes can result in severe surgeon fatigue and consequent reduction in the quality of patient care. An alternative is a hand-eye collocated digital stereo microscope, where a flat panel digital stereo display system replaces the oculars of the surgical microscope and a software programmable video processing pipeline replaces the optical processing pipeline of the surgical microscope. Though the hand-eye collocated digital stereo microscope aid is convenient, there are some concerns preventing the adoption of digital stereo microscopes. In short, unless the delay, frame rate, resolution and binocular disparity of the video frames are controlled to suit the micro manipulations done in surgery, the digital stereo microscopes cannot be used as an alternative to the existing surgical microscopes.

The first is the need of personalizing the stereo display since the perception of the depth and the degree of depth is subjective and depends on the inter-pupillary distance of the user as well as the quality of the eye. Similarly, to achieve hand-eye coordination, the delay and delay jitter should be within tolerable limits of the user. Third is the resolution of the video images that is perceived by the individual eye to produce realism and details. Since the human eye is resolution limited, resolution may be traded for other factors. However, having sufficient resolution to show the details to enable suturing on a 1 mm vessel is necessary. This could be achieved through optical magnification and sufficiently high resolution. For example, if a 20 mm×20 mm area is captured at full High Definition (HD) of 1920×1080, the resolution of a 0.1 mm spot is sufficiently resolved so that there is roughly 50 pixels denoting the area. This is sufficient for the human eye to perform suturing. The pixels gets enlarged when displayed on a display screen of 12"-15" diagonal. Lastly, the number of frames captured should be high enough not to cause blurring due to motion. Though hand movements are sluggish in micromanipulation, there is subjective sensitivity to the frame rate. A digital stereo microscope must optimize these parameters to suit the needs of the individual user.

There are many factors that restrict frame rate, cause delay, produce disparity in the left and right view images, and limit resolution. They can be optimized for a specific surgeon's eye as well as for a specific application. For example, limiting the resolution can reduce the payload to be transmitted and received through the communication links connecting the imaging device and the processing system, thereby reduces the delay. Increasing the frame rate increases the bandwidth needed to transfer video data between the imaging device and the processing system. Increasing the depth range increases the depth precision, but increases the accommodation vergence conflict and the resulting fatigue.

There exists a need for personalization systems and methods for digital stereo microscopes to optimize various parameters to the needs of an individual surgeon.

BRIEF SUMMARY OF THE DISCLOSURE

In various exemplary embodiments, a personalization method is described for a digital stereo microscope system including a camera system configured to produce a stereo pair of images, for a left eye and a right eye of a user. The personalization method includes performing a test procedure by the user with the digital stereo microscope system and providing feedback during the test procedure; testing determined parameters from the test procedure for the stereo pair of images; adjusting and correlating resolution, magnification, and disparity from the testing of the stereo pair of images; and storing the determined parameters from the adjusting and correlating as default values for the user.

BRIEF DESCRIPTION OF THE DRAWINGS

The present disclosure is illustrated and described herein with reference to the various drawings, in which like reference numbers are used to denote like system components/method steps, as appropriate, and in which.

DETAILED DESCRIPTION OF THE DISCLOSURE

Figure 1:
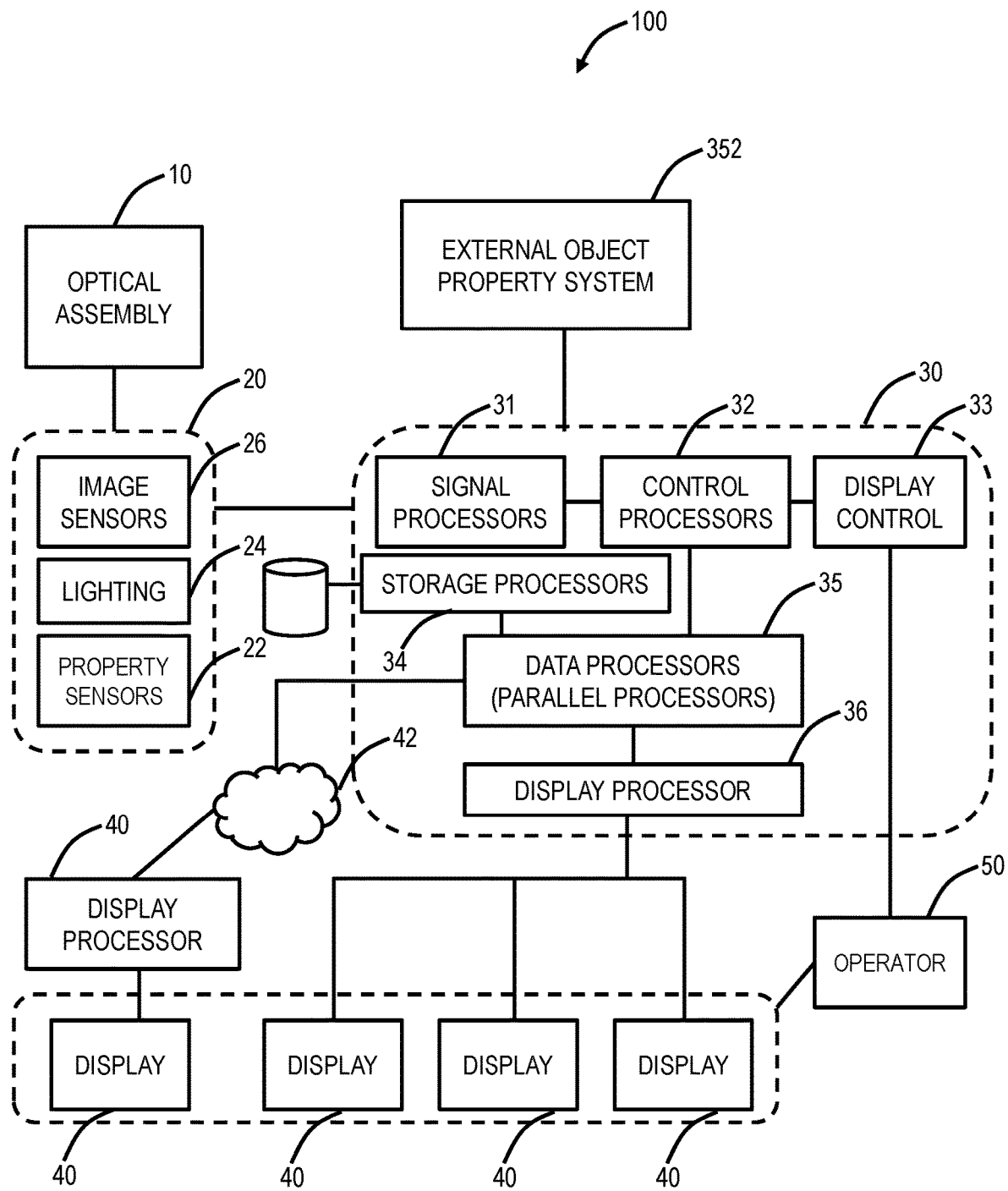
FIG. 1 describes a digital stereo microscope with image augmentation capabilities according to an exemplary embodiment.

In various exemplary embodiments, the present disclosure relates to personalized hand-eye coordinated digital stereo microscope systems and methods. The systems and methods are capable of measuring and adjusting parameters of resolution, frame rate, delay, disparity, lighting brightness, contrast, color temperature, CRI of the lighting, optimization ambient light, optimization to the angle of view to the screen, and the like to store a configuration that allows the subjectively comfortable display of information to aid surgical manipulation. The systems and methods include selecting components through fine-tuning to suit a range of users of the system for the specific application of surgical manipulation.

There are a number of factors that affect the perception of the depth and hand-eye coordination as described earlier. However, they can be classified into two, namely the measure and the variance of the measure. For example, there is a tolerable limit for the lag or delay in a system, and a tolerable limit for the delay variance or jitter. Image acquisition and processing systems are specified by associated acquisition and processing delays. However, two different systems of the same specification may have two different variances. For example, two similar cameras may produce frames at an average rate of 30 frames/sec, though there may be instances where the rate is 29.3 frames/sec or 31.7 frames per second. Such variations occur due to the variances in their components.

If stereopsis is used to provide depth sensation, depth can be sensed at small dimensions. A technique of providing stereopsis in a digital system includes a set of cameras capturing the image of the scene, transmit the image to a computer system, and the computer system adjusting the images to provide sufficient disparity and zero distortion to the viewer through a stereoscopic display and viewing system. In order to provide the operator of the system, for example, the surgeon, the required hand eye coordination, the frame rates must be sufficiently high, frame delay negligible, and frame delay variance extremely small.

Cameras are specified by their frame rate and resolution. In practice, practical cameras vary in their frame rate by small amounts. The frame delay is governed by transmit and receive times as well as propagation time governed by the link errors. Due to the varying nature of the link errors, the frame arrivals can be varied, producing varying effective frame rates. When multiple cameras are used, even when they are synchronized, there is slight error in their starting times when the frames are produced. Though these errors are small, over a period of time, due to the variance in the frame arrivals, frames from multiple cameras arrive in such intervals that the transport of the frames to a video processing engine need be done in multiple stages. Performing frame transfers in multiple operations causes inter-frame delays which causes delay jitter in the presented display. The delay jitter and delay severely disrupts the hand-eye coordination. The systems and methods described herein rectify these errors to produce a properly hand-eye coordinated system so that micro-manipulations can be made.

Also, in various exemplary embodiments, surgical stereo vision systems and methods for microsurgery enable hand-eye collocation, high resolution, and a large field of view. Multiple multimodality sensors, including image sensors, capture properties of an object under the view of the system and the user's micro manipulations of the object. The captured live view is augmented with data from sensors and external databases to aid real-time micro manipulation of the object. The system provides multiple views on one or more flat-panel stereoscopic displays, collaborative manipulation of the object, real time measurements, and panning and tilting of the field of view without moving the object. The system supports microsurgical manipulations to be performed on a patient by a group of surgeons and imparts training to surgeons by recording and replaying the surgical manipulations with a phantom object in the field of view. The system includes a Digital Stereo Microscope (DSM) that provides augmented and collocated live stereo views to rectify the limitations of conventional systems. The system uses optical elements and imaging sensors for image capture, digital computing for processing, and digital displays for stereoscopic viewing. In addition to the optical imaging, the system includes multimodality sensors and different image augmentation schemes for improving the visualization of and interaction with the operated site.

An objective of the surgical stereo vision systems and methods is to achieve Surgical Light Microscope (SLM) parity in resolution and magnification used in surgery. This includes achieving continuous zoom using a movable intermediate lens assembly between the objective lens and ocular without the use of intermediate lens assembly.

Another objective includes a reduction in viewing latency to be unnoticeable to the human eye. Due to the indirect viewing of the real scene, latency introduced between what happens at an operating site and what is seen in the video of the live interaction which may disrupt the surgical procedure.

Yet another objective is to provide better functionality than conventional SLMs and DSMs by providing scene augmentation and alternate views. Multimodality sensors and image sensors on flexible arm can be used to provide augmentation and alternate views. The video streams are stored and replayed to allow surgical training in the same environment as that of the actual surgery.

Another objective of the surgical stereo vision systems and methods is to provide better ergonomics of stereo interaction for long surgeries through a hand-eye collocated stereoscopic display with support for pan, variable zoom, and tilt of the field-of-view. Advantageously, a stereoscopic view will not be lost by moving the head. Still yet another objective is to allow collaboration in the surgery having multiple surgeons and surgery assistants to simultaneously share the live view and multiple surgeons to cooperate sequentially without causing stereopsis related delays.

Referring to FIG. 1, in an exemplary embodiment, a block diagram illustrates a digital stereo microscope system 100. The digital stereo microscope system 100 includes an optical system 10, an image acquisition system 20, a processing system 30, and an image display system 40. The image acquisition system 20 includes a collection of object property sensors 22, a collection of lighting resources 24, and a collection of image sensors 26, in data communication with the image display system 40 via the processing system 30 and connected to the optical system 10 through the image acquisition system 20. The optical system 10 captures the field of view and sends an optical image to the image sensors 26 for generation of high resolution digital image of the scene. The image sensors 26 can include, without limitation, CMOS, CCD, photo-voltaic sensors, infra-red sensing elements, and the like. The processing system 30 includes various processors such as signal processors 31, control processors 32, display control 33, storage processors 34, data processors 35, and display processors 36. The human operator 50 places the display units 341 and sensing elements 313 to yield a stereo view of the operating site using the display control 323. The lighting resources 24 are configured to provide variable amounts of visible light to the field of view. The object property sensors 22 are used to provide data to the processing system 30. The object property sensors 22 can include, without limitation, infra-red transceivers, ultra-sound transceivers, laser transceivers, light field cameras, depth sensing cameras, and the like.

Figure 2A:
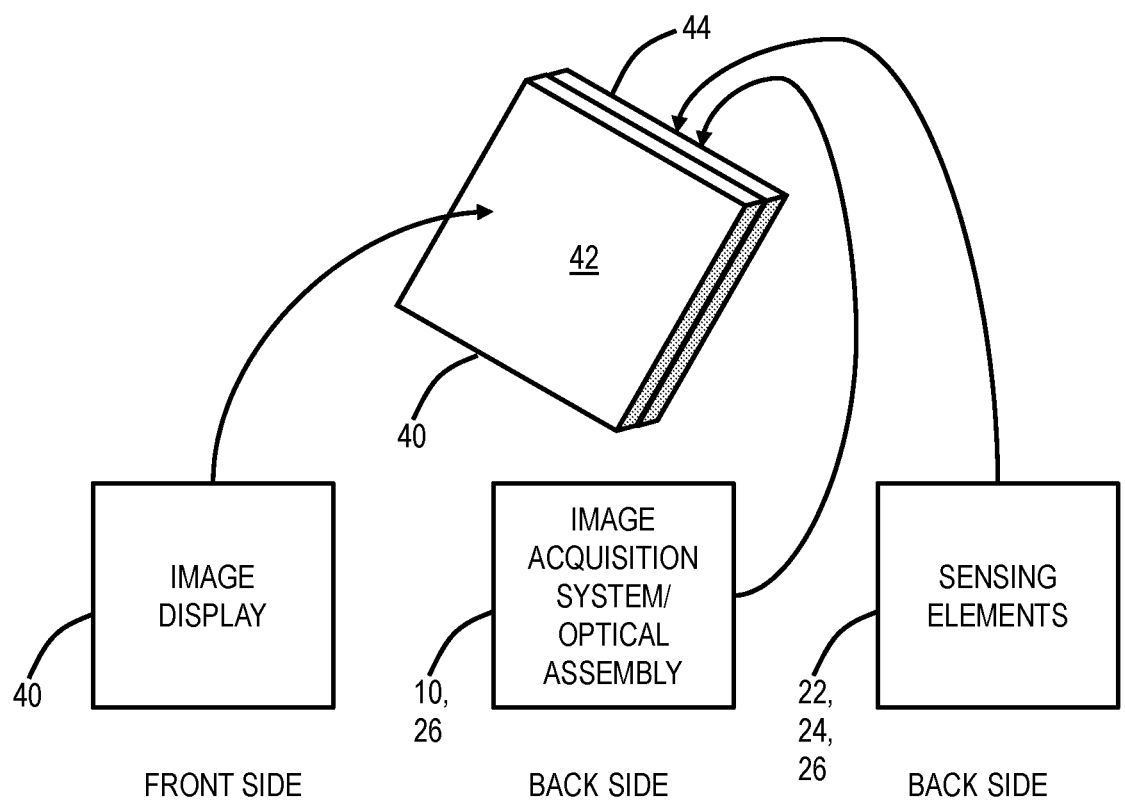
FIG. 2A describes one preferred arrangement of image sensors in the back-side of the display unit according to an exemplary embodiment.
Figure 2B:
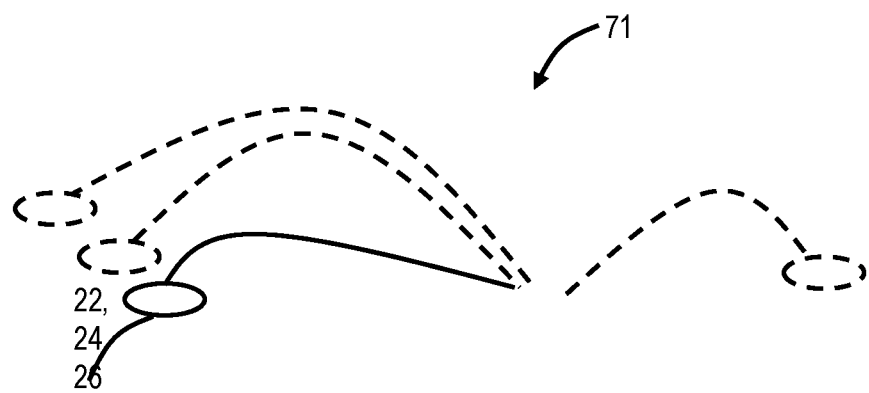
FIG. 2B describes another preferred arrangement of image sensors on a flexible arm fixed to a stand according to an exemplary embodiment.

Referring to FIGS. 2A-2B, in exemplary embodiments, a diagram illustrates a display/image sensor unit 40. In particular in FIG. 2A, components of the optical assembly 10 and the image acquisition system 20 can be disposed on a back side 42 of the unit 40 with a display unit 40 on the front side 44 of the unit 40. Further, each of the various sensing elements 22, 24 can be independently or collectively controlled by a human operator 50. As is described herein, the design of the display/image sensor unit 40 is critical to enabling hand-eye collocation as the display 40 is placed over an object of interest while hands of the human operator 50 manipulate the object of interest. The sensing elements 22, 24 may either emit sensing rays such as visible light, ultrasound or infra-red, collect sensing rays, or both emit and collect sensing rays.

Some of the sensing elements 22, 24 may be placed on a flexible arm 71 as shown in FIG. 2B and brought to an operating site. The operating site includes the field of view of the system 100 and outside the field of view of the system 100. Some of the sensing elements 22, 24 such as the visible light camera and infra-red camera may be placed on both the flexible arm 71 and the back side 42 of the display unit 40. The arrangement of camera elements and other sensors may be along a curve. The arrangements can also be along a line or along a curved surface, so as to aid increasing the field of view. The position and orientation of one or more sensing elements may be controlled by the human operator. Also, the image sensors 26, the light sources 24, and/or the object property sensors 22 can be arranged on one of the flexible arms 71 which can be moved to focus to the operating site with manual assistance. These additional sensing elements on the flexible arms 71 are used to obtain views that are not possible with zooming and panning of the current field of view. For example, the self-occluding portion of a tissue can be made visible only through an alternate angle of view. It requires either moving the patient or tilting the image sensors 26 fixed on the back-side of the unit 40. By tilting the camera, the current view of the operating site is lost, i.e. hand-eye collocation is lost with the unit 40. By having the additional image sensors 26 fixed to the flexible arms 71, alternate views can be composed within the current viewing context. Alternate views can also be obtained from the plurality of image sensors 26 arranged at the back of the display. The limited view of the DSM and SLM systems are overcome through this arrangement.

Figure 3A:
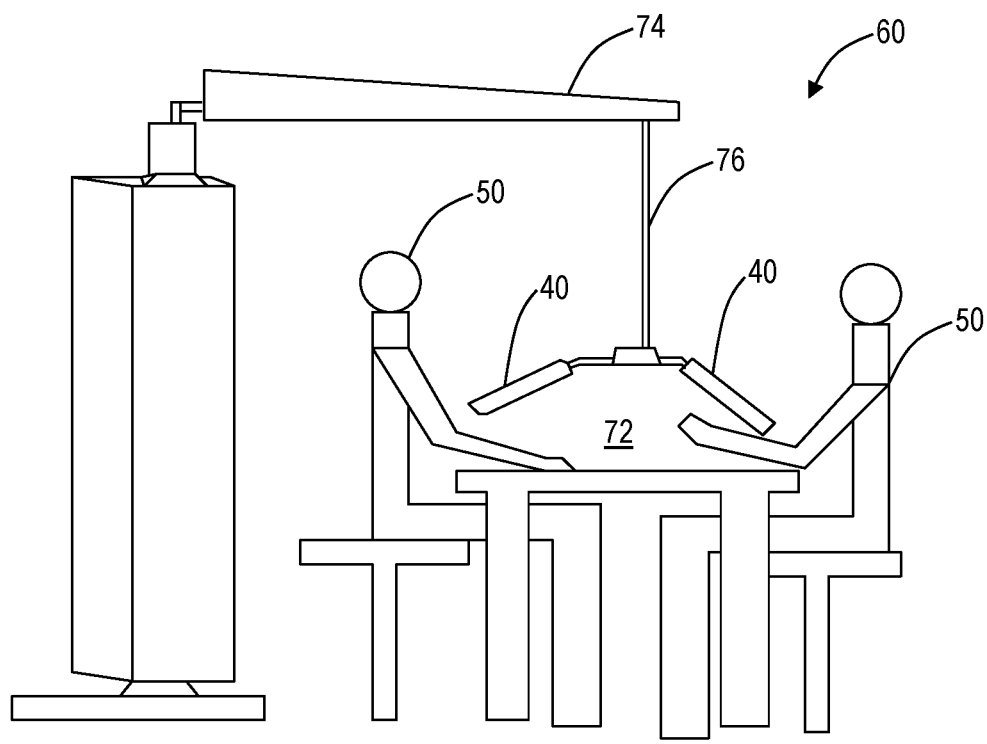
FIGS. 3A-3B describe a hand-eye collocated stereo display with FIG. 3A describing a schematic of the system with two users sharing a display and FIG. 3B describing the display arrangement and indirect viewing according to an exemplary embodiment.
Figure 3B:
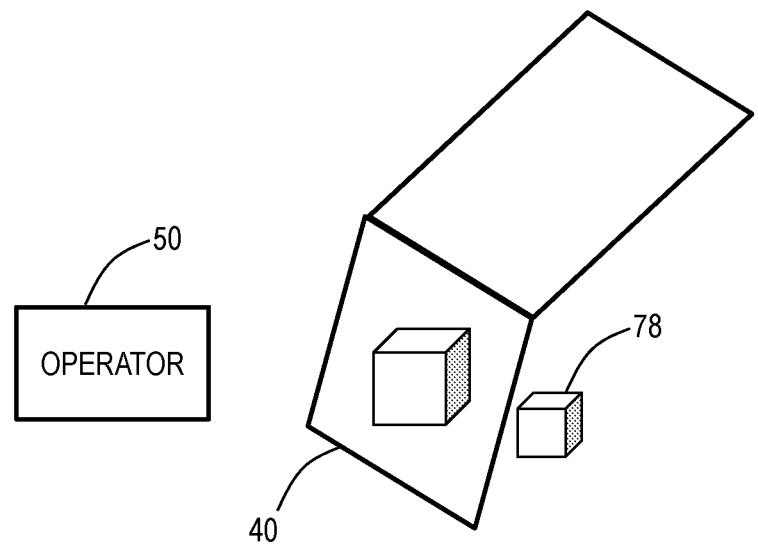

Referring to FIGS. 3A-3B, in exemplary embodiments, diagrams illustrate use of the unit in a surgery system 60 with a hand-eye collocated stereo display. FIG. 3A shows a schematic of the system 60 with two users sharing the system 60 and FIG. 3B shows the display arrangement and indirect viewing of the display unit 40. Specifically, a human operator 50 initially places the display unit 40 along with the mounted sensing elements above an operating site 72 to view the operating site 72. An anatomical view of the operating site 72 is projected onto the display unit 40 and the human operator 50 can give control commands to zoom, pan, focus, etc. The operating site 72 can be an area of interest over which the display unit 40 is located and which is magnified in the display 40 of the display unit 40.

The processing system 30 generates commands to orient one or more of the sensing elements 22, 24, 26 in response to the human operator's 50 commands. The human operator 50 may adjust the height and viewing angle of the display unit 40 without invoking the processing system 30. For example, the system 60 can include an articulated arm 74 and a display mounting system 76 that allow adjusting the position of the display 40 at convenient viewing height and angle as well as leaving sufficient working distance. Based on the human operator's 50 viewing and working distance configuration, and the indication of the operating site 72, the selection of elements 22, 24, 26 and its orientation is decided by the processing system 30.

The location of the operating site 72 may be indicated by projecting a cursor 78 onto the scene. The human operator 50 moves the cursor to the desired site. The location of the operating site 72 may also be indicated by the human operator 50 by entering the anatomical location of the operating site 72 and then perform operations of pan, tilt and zoom to select the view and desired magnification. The human operator 50 performs the pan, tilt and zoom using one or more of the following methods. The human operator 50 may use a control knob or knobs associated with the unit 40 to increase and decrease each of these parameters. The human operator 50 may use a virtual object projected on the scene to control the parameters. Multiple methods are provided for convenience and safety. The human operator 50 may adjust the disparity and the distance between the eye and the display 40 to obtain the stereo view. These finer adjustments are done using the tool tip or using the control widgets.

The system 100, 60 may be operated in three modes, the pre-operative mode where manual control as well as control knobs is used to position the system 100, 60. During the surgical operation mode, the fine controls are done using the virtual objects such as the virtual cursor, and control widgets projected onto the field of view. In the post-operative mode, a greater field of view is provided to track the tools returning to the tool chests.

The image sensors 26 can include various cameras which can be positioned in various locations in the system 100, the display unit 40, and the surgery system 60. In an exemplary embodiment, the surgical vision systems and methods operate with the various cameras each acquiring images of an area of interest at a maximum magnification and the associated reduction in magnification being done in software via the processing system 30. Of course, the surgical vision systems and methods can also rely on lens associated with the various cameras. In an exemplary embodiment, some of the cameras are fixed on the back side 42 of the display unit 40. In another exemplary embodiment, some of the cameras are configured to move, pan, tilt, etc. In yet another exemplary embodiment, some of the cameras are mounted in different locations in the surgery system 60 from the display unit, e.g. ceiling, walls, etc. In yet another exemplary embodiment, some of the cameras are movably attached to the flexible arms 71. In still yet another exemplary embodiment, some of the cameras can be in a linear or curved camera array. Of course, combinations are contemplated of the foregoing. In the various exemplary embodiments, camera position is such that a view can be obtained of the area of interest with the operator's 50 hands and/or tools in between the display unit 40 and the area of interest, i.e. the operating site 72. Importantly, the cameras are all communicatively coupled to the processing system 30 for presenting live streams which can be manipulated by the processing system 30 for display to many different users simultaneously including different views to different users simultaneously. The cameras can be collectively positioned such that the human operator 50 can maintain hand-eye collocation with the operating site.

Referring back to FIG. 1, in an exemplary embodiment, the system 100 uses two cameras (i.e., image sensors 26) mounted on the back of the display unit 40, a camera (i.e., an image sensor 26) mounted on the flexible arm 71, a processing unit collectively referred to as the processing system 30, and two display units 40 connected to the processing system 30. The processing system 30 can have several hundred processors for processing the camera generated live stream. Specifically, the processing system 30 is configured to receive data from the image acquisition system 20 and generate stereoscopic views on the image display system 40 for hand-eye collocation at the operating site 72. Stereoscopic views include one exemplary presentation on the image display system 40. Others are also contemplated for providing depth perception. While presenting stereoscopic views, the human operator 50 can use glasses for viewing the image display system 40. An exemplary description of a system using shutter glasses is described in U.S. Patent Publication No. 2010/0103247, co-invented by the inventor of the present application, published Apr. 29, 2010, and entitled "AN IMAGING DEVICE AND METHOD. Since this prior-art system uses camera configuration to generate stereo pairs, it has same physical limitations as that of the optical microscope that the field-of-view, depth-of-field and magnification are interrelated. The prior-art system gets 2 cm to 8 cm work space which is insufficient to perform surgical manipulations. The present invention eliminates those limitations.

The processing system 30 can include various processors such as signal processors 31, control processors 32, display control 33, storage processors 34, data processors 35, and display processors 36. Variously, the processing system 30 is configured to process configuration and control commands, perform storage and retrieval of object properties such as via an external object property system 352 as well as for processing the object property sensor data from the property sensors 22. The signal processors 31 communicate and control the image acquisition system 20. The control processors 32 communicate and interface with the display control 33 which communicates and interfaces with the human operator 50.

In an exemplary embodiment, the control processors 32, the display control 33, the signal processors 31, and the storage processors 34 resides in a host central processor unit or units (CPU) and the data processors 35 resides in a large number of processors attached to the CPU through an interface, i.e. a bus such as Peripheral Component Interconnect Express (PCIe). The communication between host CPU and the PCIe hosted processors can be very infrequent. In configurations where a light projector for the lighting 24 is used to augment the display 329, the host CPU provides the display signal to the projector. The system 100 can also include multiple display processors 36 connected to the data processors 35 either via the interface or a network 42 connection. The display processors 36 are also communicatively coupled to the display 40.

For initial configuration, the system 100 is powered on and the display units 40 are moved to the site of the surgery. Once stereo views are visible in the display 40, the human operator 50 picks sensors from the set of sensors presented on the display 40 and places them in the three dimensional (3D) space. When sensors are connected, the data will be displayed at those positions. Once the human operator 50 view operations are completed, the sensor icons are removed from the display 40 by user interaction.

Once the first display unit 40 is calibrated to convenience, the second display unit 40 is calibrated by another respective user to suit the view parameters. The disparity for the stereo pairs may be different for the second user; however, the camera movements are now arrested. The user operation results in building disparity computation matrix that affects only the processing of the stereo pairs. The relative camera movements suggested by the second user is factored into a processing vector which is applied to the incoming viewing pairs. When both camera units are calibrated, further fine tuning of the calibrations is possible with both display adjustments results in changes in a transformation vector. This can be repeated for additional users.

Multiple surgeons and assistants may calibrate the system to their visual comfort and store the calibration against their named icons. Then during the surgery, the respective surgeon can bring the calibration by touching and activating their stored configuration parameters. Surgeons could also be recognized by the system through biometric recognition. The transformation vector may be either stored in the local display processor 36 or in the processors 35). When the transformation vector is stored in the local display processor 36, the processors 35 fuse the information that need to be processed by the human visual system. Since the various cameras associated with the system 100, the unit 40, and the system 60 are all capturing portions of the area of interest, the processing system 30 can be used to synthesize different live views simultaneously for different displays 40. For each view the operator may choose to see the same as what the other operator is viewing or an independent view (through another set of camera) or a combination of the views on the same screen. Generally, the system 100, 60 is configured via the various components contained therein to capture a whole area from an image perspective and to synthesize each person's view on the fly via the processing system 30.

With respect to hand-eye collocation, the human operator 50 performing a surgery at the operating site 72 will see the display 40 as if the display 40 was a magnifying transparent glass without the limitations of a magnifying glass. In a basic case of no magnification, it would be like looking through a glass. Of course, the display unit 40 contemplates magnification and augmentation of the magnifying glass. However, the systems and methods described herein are not limited to a collocated view. The operator 50 can choose to view an area of interest that would not be visible if he were to look through the glass model, for example the side of the work area facing away from the operator. The system 100, 60 could have cameras arranged in such a way to image those and make them available to the operator without tilting the scope or the subject. This is a huge advantage in surgery. Even with the direct collocated view, there will always be occlusion due to the operator hand and tools hiding the work area. Once again cameras can be placed (multiple statically placed cameras on a plane or a curved surface or few cameras that are moved electronically using motors) such that the occlusion can be minimized.

Composing the signal information from the image acquisition system 20 with the live stream displayed on the display system 40 involves a two-step process. In a first step, the information is streamed into the processing system 30 including device memory and processors that are responsible for the portion of live stream data indexes the signal information and fuse them into the common display. A second step includes performing various processing techniques bon the information by the processing system 30 prior to sending the processed information to the display 40.

The system 100 can be controlled by contact and non-contact means. Tool tip position and gesture are used to enter into command mode. For example, during a surgery, surgeon needs to change the magnification or select an opposite view. Surgeon can move the tooltip to a plastic reference object placed in the field of view of the microscope and having a specific pattern and touches it. This switches the system 100 to command mode and brings up virtual widgets which can then be chosen based on gestures. Magnification of widget overlay is controlled by up/down movements of the tooltip in command mode. Similarly, for camera selection, the widget brings up a palette of cameras and user selects them by movement. The tooltip and the virtual object must be easily recognized from video stream and should be prioritized in the data processing.

Another control operation is that a user annotates an object in the visual field using a tool tip for sharing information for future use to aid a collaborating user. The annotation may also may be an instruction to the collaborating user and used immediately. For example, an operator is able to measure angles and distances in the visual field between identified points and identified lines.

In another control operation, the user may pan or tilt the field of view or zoom a selected sub-field of the field of view. For example, a surgeon may want to see a portion of the current operating site occluded by a tissue. An alternate view can be requested without moving the patient. In another example, the surgeon may mark a portion of the tissue in the command mode and request it to be zoomed. The zoomed portion may be displayed as an overlaid or as a separate a picture in a designated portion of the screen.

The system 100 contemplates various methods for command input by the human operator 50, such as hand interaction, foot pedals, etc. Also, gestures are contemplated in the area of interest, i.e. by the operator's 50 hand or tools. For example, the operator 50 can use ordinary surgical tools for issuing commands to the system 100 in addition to the foot pedal based control or the like. This could be done by say first touching a special unique object in the field of view and thereafter using tool gestures. The operator 50 returns to normal mode by once again touching the special object.

In an exemplary embodiment, the display 40 can provide a high definition stereoscopic display of the field of view, and can include a 1920×1080 pixel stereoscopic display. The display 40 can also display additional special elements. For example, the display 40 may show control widgets in a designated portion of the display 40 and movements in this portion of the display is treated as commands. The display 40 may also contain object properties as detected by the property sensors 22. For example, the temperature at an operating site may be displayed in a separate area. It may also be displayed as an overlay.

The display 40 of one user may be different from the display 40 of another user. For example, a user may choose to perform pan, tilt and zoom and see a different display than the collaborator in a special display mode. In the normal display mode, all views are shared.

In an exemplary embodiment, the zoom levels available in the system 100 are from 6× to 12× though only a magnification of up to 5× is used commonly in surgery due to the dexterity limits of human hand. Higher magnifications are useful for robot guided surgery or other applications. The system 100 contemplates use in manual surgery, and manual surgery with tremor reducing devices which limit the operable magnifications.

Another type of magnification occurs when the system 100 uses a Complementary metal-oxide-semiconductor (CMOS)/charge-coupled device (CCD) sensor. The CMOS/CCD sensor can be 5 cm×5 cm in dimension with 1920×1080 pixel read out for display on a 22 inch screen of 1920×1080 pixels. The scale factor is of the order of 5 without using optical zoom. In addition, optical zoom may be employed to increase the magnification of selected tissue sections for surgeon's view.

The system 100 overcomes many data processing and transmission challenges in conventional systems. For example, the system 100 constructs a stereo view and let the human visual system compose a 3D object through stereopsis. A very high resolution of the live image stream is necessary for faithful reproduction of the 3D object in fine details. Especially, in microsurgery, where surgical manipulations are done on a highly magnified object, the distortions are minimized to gain fine details of the operating site 72. The resolution requirement increases with the magnification required. For a magnification of 3×, the high definition (HD) resolution (1920×1080 with 24 bits deep) is the minimum required. The number of frames from the camera sensors can be at 30 frames/sec, giving rise to 30×1920×1080×3 bytes, which is approximately 178 MB~200 MB per second per sensor. With an average of four camera sensors active at the same time, 800 MB/sec bandwidth is necessary. The high bandwidth requirement causes many challenges. The number of memory transfers that are permitted in a frame operation must be limited to avoid causing delays.

For example, if the memory bus is 512 bits wide and memory clock is 1017 MHz and are using double data rate RAM, then the peak theoretical memory throughput is 1017×106×512×2/(8×10243)~130 GB/sec. The theoretical transfer rate is not achieved, because it assumes a single memory transaction with negligible setup and terminates costs. It only serves as a guide. In practice different elements of the memory segments are accessed and based on the access pattern, the number of memory transactions needed is much higher. Hence algorithms that process to produce stereo pairs are used to have aligned memory access for the device to reduce the number of memory transactions.

Another problem is the computation needed to perform operations on the stereo pairs. Stereo pairs are produced by two cameras, each of focal length f, fixed on a baseline with a baseline distance B apart and collects incident light on an object placed at a distance D. The two cameras will produce the image pixel which differs by a distance d for the point object.

$$D = \frac{Bf}{d} \qquad (1)$$

The point object produced two image points, one for the left image and another for the right image. Their difference in their position in the image is an indication of the relative depth of the object. Finding the corresponding points in each of the images and thereby finding the disparity or the relative horizontal shift is essentially the stereo computation problem. The problem is solved by finding the pixel with least difference in intensity. This is an extensive computation requiring large CPU resources and high memory bandwidth.

Typically, find the SSD (sum of squared differences) between the right and left image intensities to identify the pixel correspondence in the pixel arrays L and R corresponding to the left and right images. For each pixel, the minimum SSD value indicates a candidate correspondence pair. The computation is nearly impractical to be done at live streams at high resolutions such as HD resolution.

$$SSD_{x,y} = \Sigma_{i=x-w}^{x+w} \Sigma_{j=y-h}^{y+h} (L[i,j] - R[i-k,j])^2 \qquad (2)$$

If the pixels are to be corresponded, then the stereo images must be searched for sum-of squared distances. In addition, differences in the focal length of the two cameras, the lighting, can all contribute to ambiguity in determining correspondence in the image plane. For live streaming of stereo, the difficulty is in performing the processing in real time. The present system 100 uses selective processing of regions to avoid delay. The regions that need to be updated more frequently are processed by more number of processors in the processing system 30. Specifically, the selective processing can include uniquely patterned objects in the subject area (e.g., patterned clothes, reference frames, tools, etc.) to help match the two views. That is, the system 100 can make use of the constraints associated with the operating site 503 for additional information that can be used to make fast-uniquely patterned objects in the subject area to help match the two views.

Also, the system 100 can include techniques that inflate the depth perception on a gradient with a focus point as its center. The idea is to have greater clarity at the focal area and gradually decreasing clarity at areas further away from focus. This allows for speed and processing efficiency while focusing where it is important, the focal area of the operating site 72.

The system 100 offers special operations such as removing occlusion of the tissue due to bleeding by selecting the IR camera sensor elements and processes the streams originating from both IR and visible light sensing elements.

As described herein, the processing system 30 can be divided into five data processing modules, the signal data processors 32, the control data processors 32, the image data processor 35, the storage processors 37, and the display processors 36. The display control 33 module is also part of the processing system 30. The signal data processors 32 receive, via the elements 22, 24m, non-image sensing elements of the digital microscope as well as vital signals from other sensing elements that are not part of the digital stereo microscope. The received signals may indicate the current temperature of the operating site or pressure, pulse rate, ECG etc. These are monitored by functional specialists and the surgeon may be informed. When such information needs surgeon's attention, it can be brought to surgeons view by projecting the information into operating view of the surgeon and away from the operating site.

Information such as signal data, measurement data, and control widgets may be projected into the operating site by combining the images by an image processor 105 into a single stereo pair of images send to the display unit. Alternatively, such information may be projected by a tiny projector mounted on the back side 42 of the display and the combined image stream may be processed by the image data processor.

The system 100 can fuse a selected sensor stream of surgical motion and fuse it with the image of the surgical site to simulate conditions of actual surgery by using the training surgical specimens mounted at the operating site.

In addition to the camera and lighting elements mounted on the back side 42 of the display unit 40, a number of camera and lighting elements are provided in a spoke-and-hub arrangement, mounted on the flexible arms 71 to provide alternative views of the operating site 72. The image data processor 35 combines these newly presented views with the views from the camera elements mounted on the back-side of the display units 40 to provide views from a different angle.

The operating surgeon is able to perform virtual tilting of the patient using the views of the images produced by the spoke-and-hub camera system. The surgeon virtually tilt or roll the patient by using a virtual control widget which results in combining the views from multiple of the spoke-and-hub camera system.

The image data processor 35 is able to compose sets of image stereo pairs using multiple image views from the sensing elements both from the display mounted sensing elements and from the spoke and hub sensing elements. The display unit 30 is optionally able to perform adjustments to the received stereo pairs when all display units are receiving same stereo pairs.

Registration and calibration of the system 100 can be performed before the surgery by using a phantom object to establish the relationship between multiple sensor elements are their current positions. It may also be achieved with a real object or a marker placed in the field of view. Along with position of the imaging, property sensing elements, the correspondence between the object coordinates and image coordinates is achieved through registration of a fixed marker in the field of view of the microscope.

The live video data, signal processing data, object property data, and collaborating user's input are to be combined into the same virtual space and presented in the stereoscopic display 30. There are different processing steps. In a first step, the video data from multiple cameras are clipped for overlapping pairs of views and corrected for matching disparity. The disparity must match the XY zoom. The combining of other data is performed in one of the following ways. In one method, a light projector projects the data into the correct locations so that the live view will have the combined data. In another method, the combining of the data is performed by the data processor 35.

The data processor 35 divides the entire data into predefined chunks. The definition of division may be based on auxiliary input signal such as motion tacking, or may be based on static division such as gradation of the visual field. Division may also divide the visual field into the operating field and command field. Some of the data are to be processed faster than the other data. For example, the command field data must be processed before the operating field. Based on the nature of the data, each chunk of data is given a collection of processors.

Figure 4:
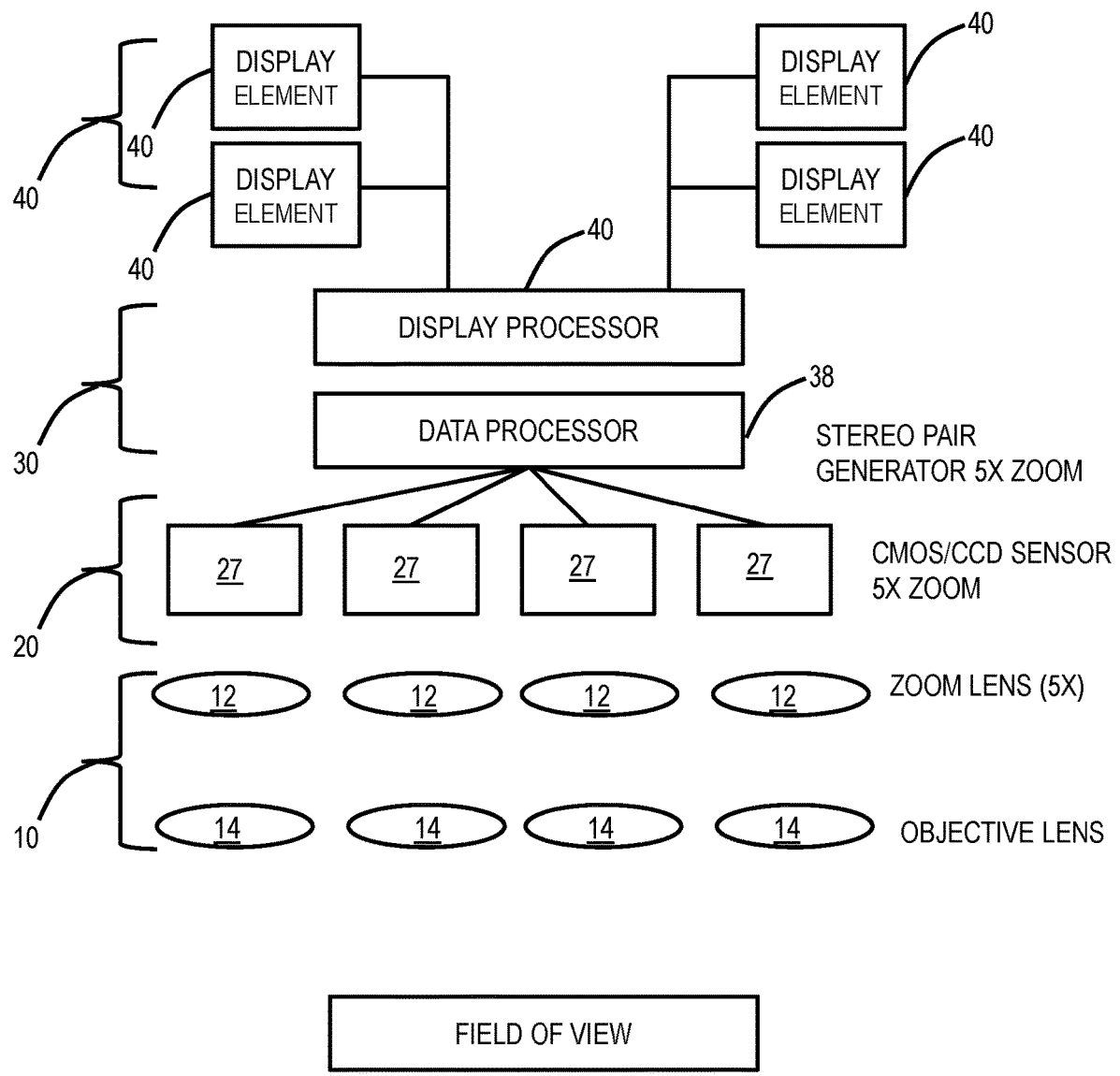
FIG. 4 describes a multi-camera system achieving high magnification and high resolution using an optical lens assembly, an image sensor, a display frame processor and a flat panel display according to an exemplary embodiment.

Referring to FIG. 4, in an exemplary embodiment, a block diagram illustrates components of the system 100 interworking with the display unit 40. The image acquisition system 20 can include CMOS/CCD sensors 27 mounted on the display unit 40. The optical system 12 can include zoom lenses 12 and objective lenses 14 mounted on the display unit. These components 27, 12, 14 can provide image data from the operating site 72 to the data processors 35 which performs processing to form stereoscopic views which are provided to the display processors 36 for display on the displays 30 on the display unit 40.

Figure 5:
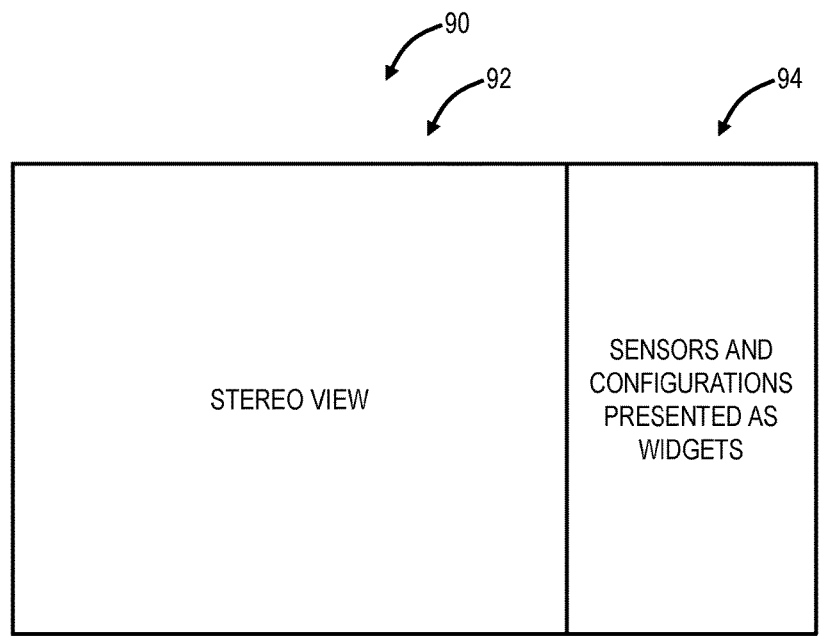
FIG. 5 describes the user interface for configuring the digital microscope.

Referring to FIG. 5, in an exemplary embodiment, a screen diagram illustrates a screen shot 90 of the display 30 of the system 100. As described herein, the screen shot 90 can include a stereo view 92 of the operating site 72 as well as other data 94 which can include sensors and configuration data presented as widgets on the screen shot 90.

There are several advantages to the system 100. Advantages are presented for the system 100 used in performing micro-surgery though similar advantages will be present in other applications. Since the system 100 allows hand-eye-collocation, both the gaze and hand movement are coordinated and eye gaze is towards the hand movement, the surgeon's strain is reduced.

Large field of view is presented to the surgeon through the stereoscopic flat display panels that allows head movement without losing the stereoscopic view. The field of view could have a uniform resolution or a graded resolution. The large field of view takes away the need for constant zoom-in-zoom-out needed to maintain context. The stereoscopic view is immediate and does not need training.

Since the system 100 does not require intensive training to perform surgical operations by looking through a microscope and adjusting the microscope positions on the fly, it can be used in other surgeries where the surgeon is not trained in microsurgery. The system 100 improves the visibility of the operating area. An example is surgery of the eyelids practiced by cosmetic surgeons.

Another advantage is the display of critical patient information such as heart rate, which can be displayed either as direct numbers or as levels along with the same display unit or as a graph. This information may be displayed at a depth in the field of view of the surgeon, but without obstructing the view of the operating site. Other pre-surgery imagery of the operating site may also be overlaid with the live stream with correct alignment to aid in the surgery.

The live stream may be processed to provide guidance in terms of mensuration and anatomical recognition. A Surgeon is able to change the view angle without moving the patient and is able to have views from different angles at the same time. The system 100 offers a platform for integrating sensors and a method of combining the sensor information with the live video of the surgery. The hand movement of the surgeon and the live video stream of the hand movement are displayed without noticeable delay, the surgeon gets a feel of the real operating site as if the display units were not present. An expert can cooperate in the surgical procedure from a remote site with some delay in the hand movements and its video stream and provide instructions to the operating surgeon.

The remote collaboration feature also offers teaching facility wherein the expert surgeon conducting the operation can be mimicked by each of the training surgeons who have the display units with the remote stereo views being integrated with the local movements. In such applications, the display unit is able to perform simple stereo image transformations to combine the scenes by adjusting the camera positions and overlaying the received images and local video. During operation, the surgeon is able to operate the system using virtual configuration objects. This satisfies the sterile requirement of the operating environments. Surgeons can use saved configurations to bring the stereo display to their own preferred settings, when multiple surgeons time multiplex during a long duration surgery.

In an exemplary embodiment, a digital stereo microscope apparatus includes a display unit located over an area of interest such that a human operator places hands and/or tools in the area of interest and views a magnified and augmented live stereo view of the area interest with eyes of the human operator having a view substantially collocated with the hands and/or tools of the human operator; an image display located on a first side of the display unit providing the magnified and augmented live stereo view; an optical system and an image acquisition system located in part on a second side of the display unit providing image capture and data capture of the area of interest; and a processing system communicatively coupled to the image acquisition system and the image display providing the magnified and augmented live stereo view to the image display based on the image capture and the data capture of the area of interest from the optical system and the image acquisition system, wherein the optical system and the image acquisition system is configured to provide the image capture with adjustments to provide the magnified and augmented live stereo view performed by the processing system.

In another exemplary embodiment, an operating system with a digital stereo microscope includes an articulated arm comprising a display mounting system; a display unit connected to the display mounting system; an operating site over which the display unit is located such that a human operator places hands and/or tools in the operating site and views a magnified and augmented live stereo view of the operating site with eyes of the human operator having a view substantially collocated with the hands and/or tools of the human operator; an image display located on a first side of the display unit providing the magnified and augmented live stereo view; an optical system and an image acquisition system located on a second side of the display unit providing image capture and data capture of the operating site; and a processing system communicatively coupled to the image acquisition system and the image display providing the magnified and augmented live stereo view to the image display based on the image capture and the data capture of the operating site from the optical system and the image acquisition system.

In yet another exemplary embodiment, a method using a digital stereo microscope includes positioning and adjusting a display unit above an operating site; enabling the display unit, wherein the display unit comprises an optical system and an image acquisition system located on a side of the display unit adjacent to the operating site, and wherein the display unit comprises an image display on a side of the display unit opposite to the side facing the operating site; providing image capture and data capture of the area of interest via the optical system and the image acquisition system; processing the image capture and the data capture via a processing system; positioning a user's hands and/or tools in the operating site while maintaining the user's eyes having a view in a collocated manner looking at the image display; and presenting a magnified and augmented live stereo view of the operating site via the image display based on the processed image capture and the processed data capture of the area of interest from the optical system and the image acquisition system.

Figure 6:
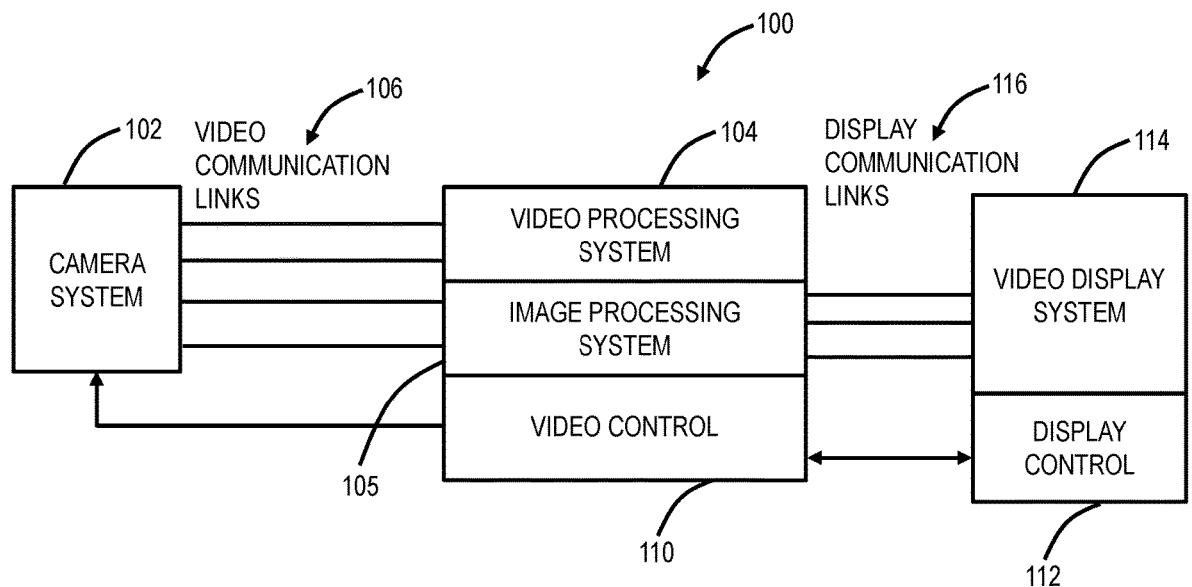
FIG. 6 describes a block diagram of a digital stereo microscope system.
Figure 7:
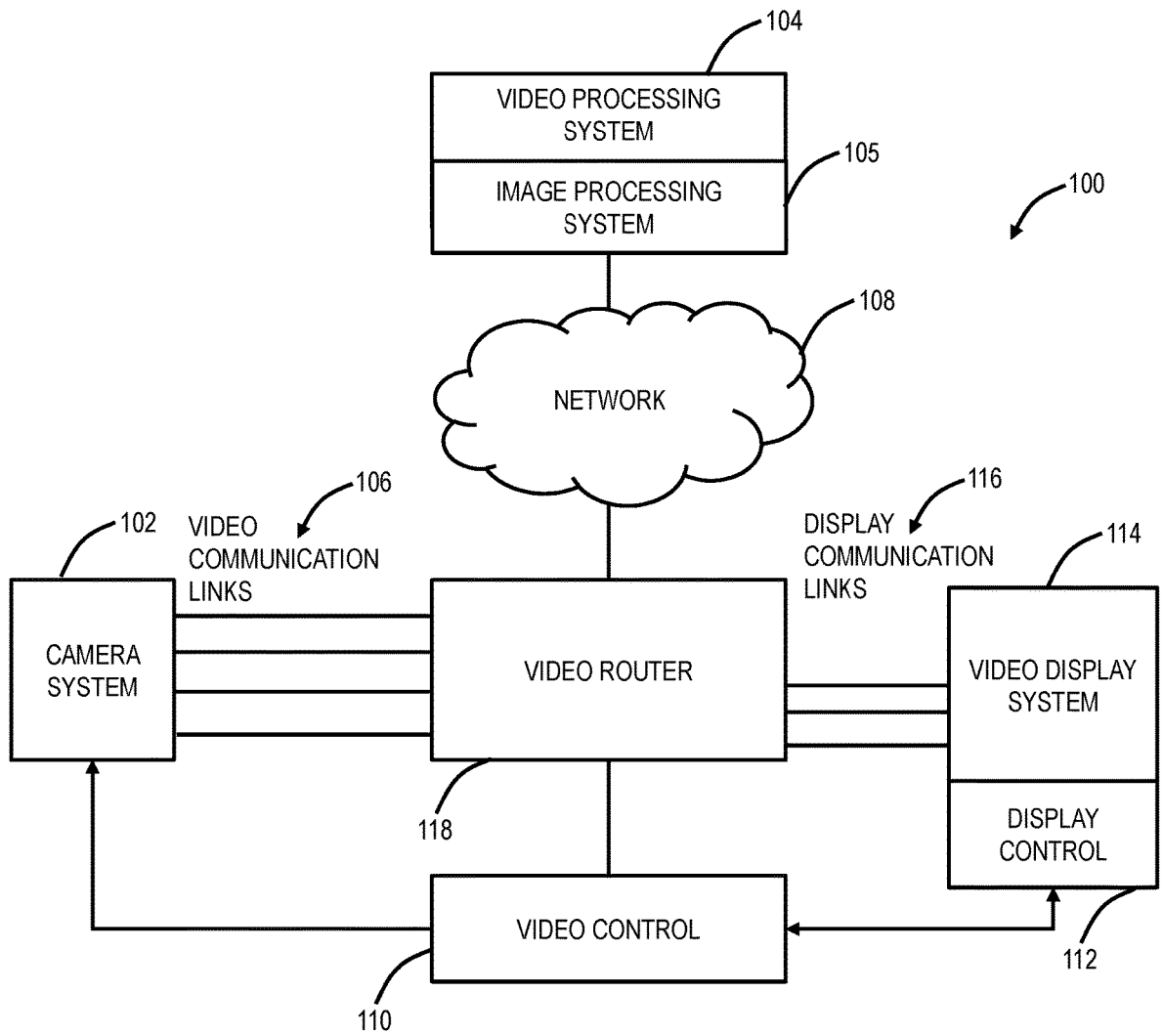
FIG. 7 describes a block diagram of the digital stereo microscope system with a remote processor.
Figure 8:
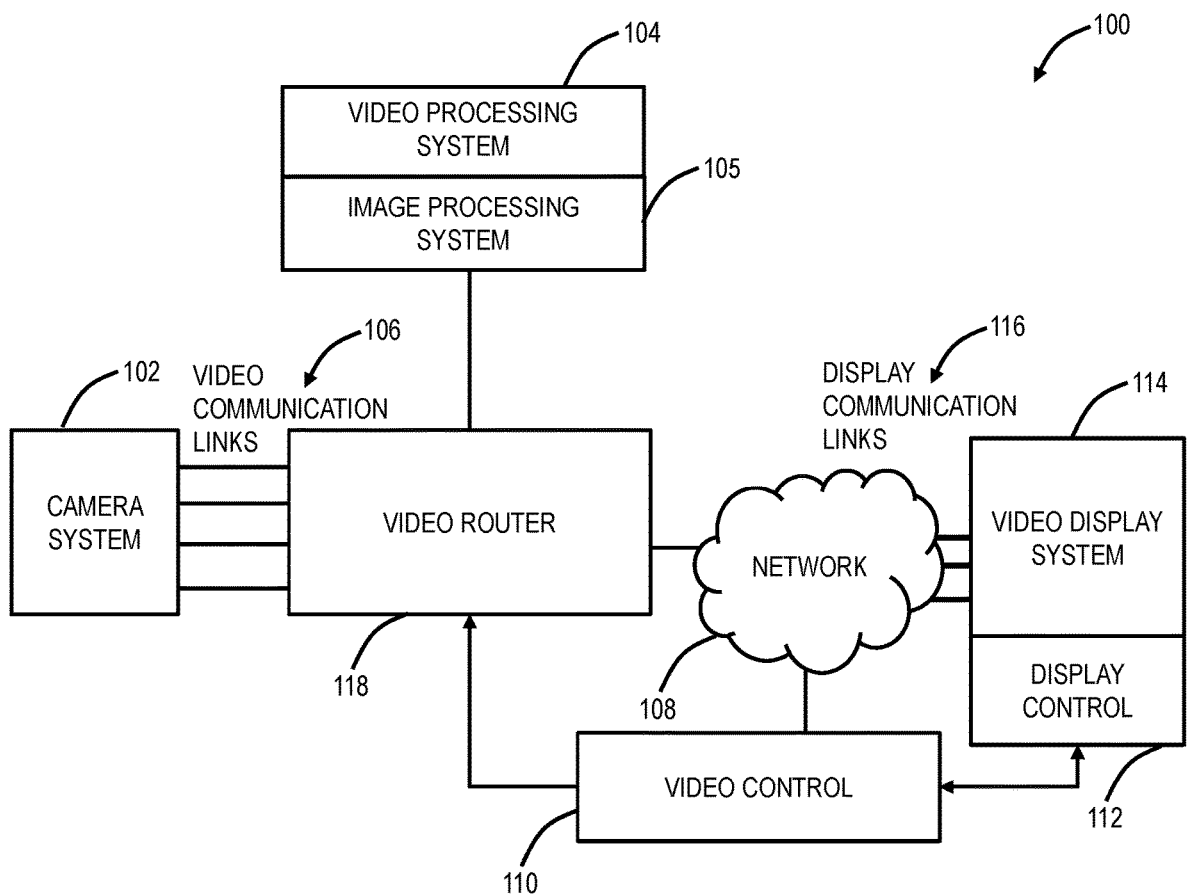
FIG. 8 describes a block diagram of the digital stereo microscope system with a remote display.
Figure 9:
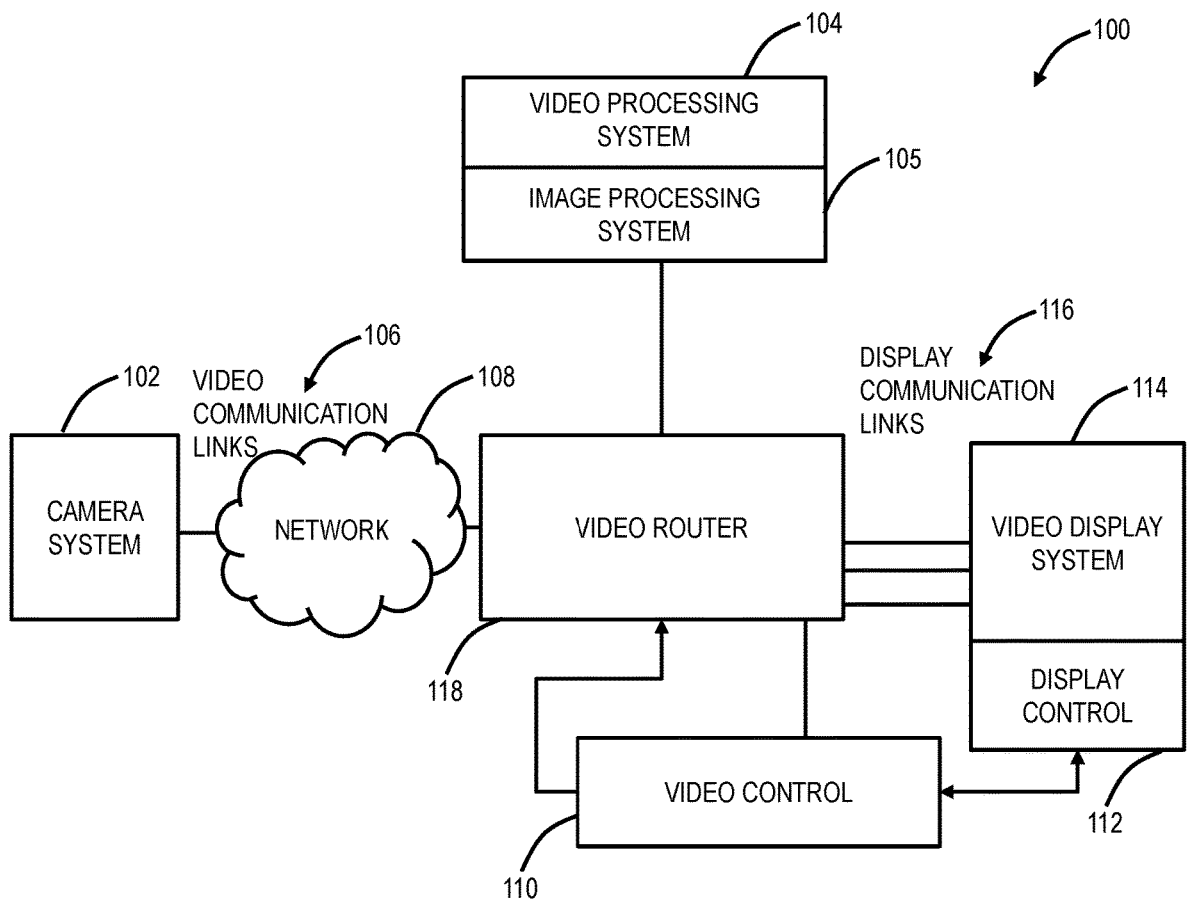
FIG. 9 describes a block diagram of the digital stereo microscope system with a remote camera.
Figure 10:
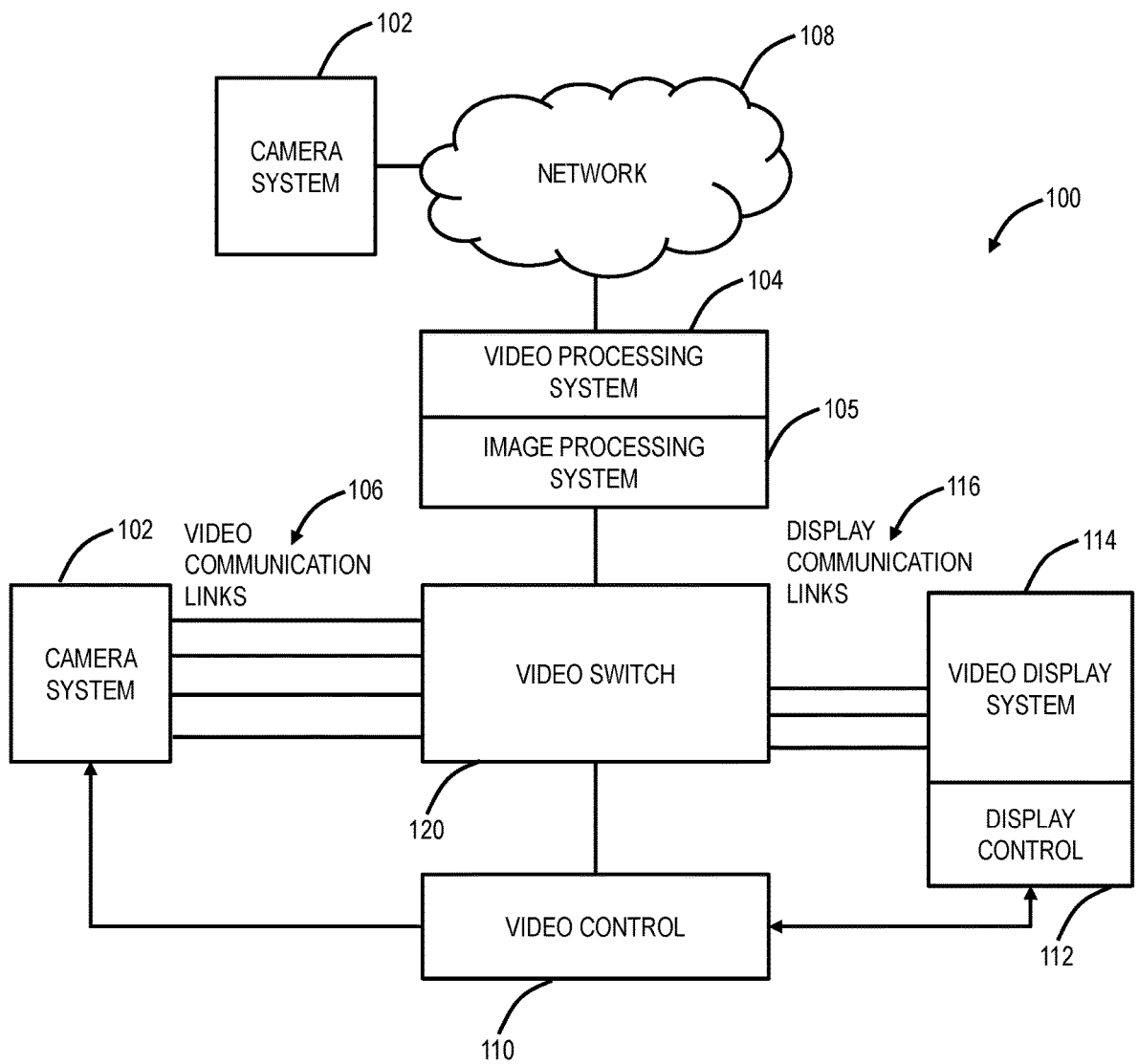
FIG. 10 describes a block diagram of the digital stereo microscope system with a selectable input.

Referring to FIGS. 6-10, in exemplary embodiments, block diagrams illustrate a digital stereo microscope system 100. FIG. 6 is a block diagram of the digital stereo microscope system 100. FIG. 7 is a block diagram of the digital stereo microscope system 100 with a remote processor. FIG. 8 is a block diagram of the digital stereo microscope system 100 with a remote display. FIG. 9 is a block diagram of the digital stereo microscope system 100 with a remote camera. FIG. 10 is a block diagram of the digital stereo microscope system 100 with a selectable input.

The digital stereo microscope system 100 includes a camera system 102 with a number of cameras, two of which are used to create a stereo pair of images. Specific cameras in the camera system 102 are selected to obtain a special aspect of the work space. The camera system 102 is connected to a video processing system 104 and an image processing system 105 through a communication link 106. The communication link 106 can be Universal Serial Bus (USB), Firewire, Low-voltage differential signaling (LVDS), High-Definition Multimedia Interface (HDMI), Ethernet, etc. Depending on the specific technology and the transmission speed offered, the transmit times will vary. For example, to transmit a 1080p video frame which is YUV2 compressed requires 1920×1080×8 bits to be transmitted. Many commercially available USB 3.0 links have a link speed of 1-3 Gbps though the theoretical link speed is about 5 Gbps. Assuming a link speed of 1 Gbps, the delay encountered in transmitting the frame is 1920×1080×8/1000 microseconds, which is approximately 16.6 milliseconds. At the frame receiving end, the time required to receive the frame is similarly 16.6 milliseconds. When the connection is a direct connection, as in FIGS. 6-8 and 10, the propagation delay is negligible. However, when the camera system 102, the video processing system 104, and the image processing system 105 are connected through a network 108, there will be significant propagation delay, as in FIG. 9. Note, while the video processing system 104 and the image processing system 105 are shown separately, these processing systems can be in a single processing apparatus.

Video control 110 is communicatively coupled to the camera system 102 for control thereof and to display control 112. The display control 112 controls a video display system 114, such as the display/image sensor unit 40. The video display system 114 receives images from the video processing system 104 via display communication links 116. The video control 110 can be part of (FIG. 6) or communicatively coupled to the video processing system 104 through a video router 118 (FIGS. 7-9) or a video switch 120 (FIG. 10).

In an exemplary embodiment, the camera system 102 is configured to produce a stereo pair of images, captured in real-time, matching an interpupillary distance of a user.

Figure 11:
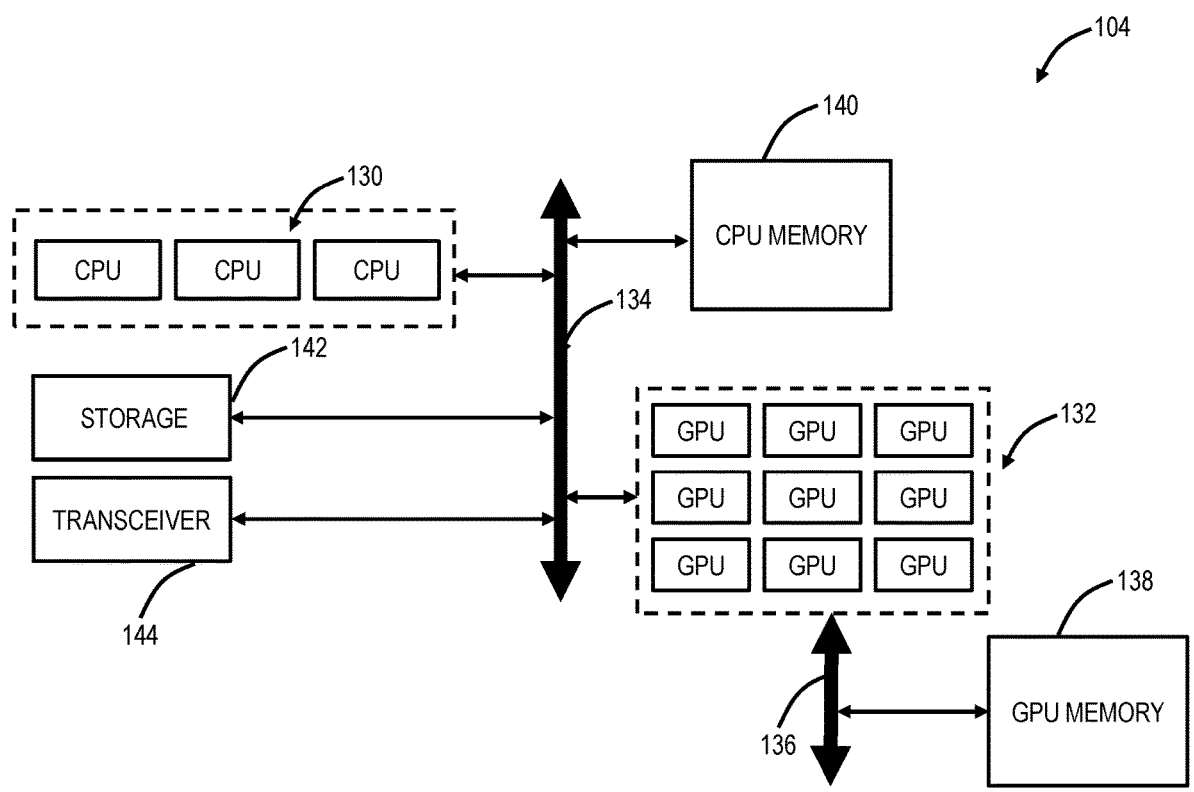
FIG. 11 describes a block diagram of an exemplary implementation of the video processing system.

Referring to FIG. 11, in an exemplary embodiment, a block diagram illustrates an exemplary implementation of the video processing system 104 and/or the image processing system 105. The video processing system 104 can include one or more Central Processing Units (CPUs) 130 and one or more Graphical Processing Units (GPUs) 132. The GPUs 132 can be coupled to the CPUs through a peripheral interconnection 134 such as PCIe. Various other components may include an interconnection 136 between the GPUs 132 and GPU memory 138, CPU memory 140 coupled to the interconnection 134, storage 142 coupled to the interconnection 134, and a transceiver 144 coupled to the interconnection 134. Data received by the CPUs 130 can be placed in the GPU memory 138 for processing by the GPUs 132. This require transferring the memory buffers from CPU to the GPU and may incur delay. The delay depends on the size of the data being transferred (depends on the resolution of the video frame) and the bandwidth of the peripheral connection.

The video display system 114 refreshes the left and right eye views at a fast rate, such as 120 Hz or the like, so that human eye perceives it as observing the real scene of the object that the images represent. The binocular disparity introduces the sense of depth. Viewing of the left and right images can be aided by an eye glass shutter which alternately closes the left and right eyes by changing the transparency of the glasses. The eye glasses can be synchronized with the video display system 114. Along with the video display system 114, there is a mechanism to control the display. The display control 112 may be in the form of a foot pedal and a configuration displayed on the video display system 114 so that the attributes of the images may be controlled. It may alternatively be a gesture recognition system so that the displayed information may be modified either in content or in the format or both. The display control 112 communicates with the video processing system 104. The video display system 114 may be directly connected to the video processing system 104 or may be connected through the network 108. The delay and the rate of the frames are made sufficient for the human eye to visualize the real scene without ambiguity.

Back in FIGS. 6-10, the digital stereo microscope system 100 may be configured in many ways. In FIG. 6, the camera system 102 is directly connected to the video processing system 104 and the image processing system 105 through the communication link 106, such as USB 3.0, and the video display system 114 is directly connected to the video processor system 104 and the image processing system 105 through DVB for data and a USB for control functions. In FIG. 7, the video processing system 104 and the image processing system 105 is away in the cloud and is connected through the network 108. In FIG. 8, the display system 108 is remotely placed and connected through the network 108. In FIG. 9, the camera system 102 is remotely placed and connected through the network 108. In FIG. 10, the video display system 114 accepts input from the camera system 102 as well as from the video processing system 104 and the image processing system 105 with an intervening video switch 120 that switches frames from the video processing system 104 and the image processing system 105 and the camera system 102

The digital stereo microscope system 100 includes the camera system 102 configured to produce a stereo pair of images captured in real-time; the image processing system 105 communicatively coupled to the camera system 102 and configured to extract the stereo pair of images synchronized in time with each other and to combine the stereo pair of images with encoded images of differences between the stereo pair of images; and the video processing system 104 communicatively coupled to the image processing system 105 and configured to create a stream from the encoded images by processing the encoded images based on personalization for the user, wherein the personalization is determined for to a user's stereo acuity based on a test procedure. The digital stereo microscope system 100 can further include a display monitor 114 configured to receive the stream for display by a programmable shutter glass worn by the user. The personalization for the user's stereo acuity can include a predetermination of monocular quality images and the interpupillary distance for the user.

The camera system 102 can include an array of camera pairs, and wherein a specific pair is selected based on the interpupillary distance and the monocular quality images of the user. The user's stereo acuity is based on matching interpupillary distance to stereo disparity on a display. The microsurgery can include a micro-suture and the personalization is performed by initially setting magnification, resolution and focus of the digital stereo microscope system 100 so that the suture is visible, wherein initial settings are recorded, and operation of one or more test procedures. The personalization can be based on a type of microsurgery and associated biological tissues involved, tools, and materials. The personalization can be based on adjusting the stereo pair of images based on the user's dominant eye.

Personalization includes matching interpupillary distance (IPD) to the stereo disparity on the display 114. A persons stereo viewing ability has parameters from the interpupillary distance, to ocular muscle abilities, to processes that are deeply within visual cortex. Collectively, the degree of ability to perceive stereo can be called stereo acuity. Apart from pathological situations, this ability varies from person to person. Movie theatres and movie producers model the average user when they produce the content and configure the theatre. It would not be possible to customize it to individual person in the theatre. As a result, the 3D has not really caught on.

The digital stereo microscope system 100 addresses this challenge by making the content and presenting the content with custom configuration that matches the stereo acuity of the person. The digital stereo microscope system 100 estimates the stereo acuity not just based on the IPD but based on a task performance based adjustment. Two people may have the same IPD, but different stereo acuity because of lazy muscles or lack of processes in the visual cortex. Or two people may have different IPDs and the same visual acuity. A clinically equivalent task based approach allows the digital stereo microscope system 100 to match the setting to the best comfortable setting for the surgeon. This is important as the surgeon needs to perform critical tasks and for a long duration. Without such matching, the surgeon will easily fatigue or in the worst case become ill. The stereo acuity also improves with increased usage of the digital stereo microscope system 100. Surgeons are allowed to make use of the increased acuity in the digital stereo microscope system 100 by tweaking the parameters through an interface. There are other elements to a surgeon's preference than stereo acuity. Visual preference varies, perception of and comfort with color, illumination brightness, illumination color temperature, contrast (both biological tissue, and biological tissue and tools/material), glare tolerance (tolerate more glare for the sake of greater contrast), viewing angle, global spectrum filters, dynamic filters and other factors also influence the performance of the surgeon. The digital stereo microscope system 100 takes these into account with a task based performance that includes a training system and other targets.

The digital stereo microscope system 100 can be customized for the procedure at hand. For the same surgeon, different procedures due to the biological tissues involved, the tools and material (such as sutures) used can benefit from a setting that matches the procedure. This customization uses the surgeon's personal preference as a base and then tweaks it to match the procedure and can be done at the site. The digital stereo microscope system 100 will also have certain procedure based presets (like digital cameras have presets for snow, fireworks, sunny day, portrait mode, sea, etc.) that surgeons can use and adapt. The digital stereo microscope system 100 will take these two preferences (i.e., surgeon personalization and procedure bases customization) and merge them to provide the best settings that allows surgeon performance for extended usage. The merging algorithm has weights assigned to parameters learned from the personal customization. The presets for procedures can also be part of the task based personalization where the tasks presented simulate the typical procedure variety.

Another area of personalization is based on identifying and adjusting to the dominant eye of the surgeon. This allows us to have the left view and right view differ not only in the stereo disparity but also in the emphasis of visual content. Since the visual cortex combines it with preference of certain content from a particular eye than the other, the digital stereo microscope system 100 can exploit that to further enhance the comfort.

In an exemplary embodiment, the various processing systems in the digital stereo microscope system 100 include memory storing instructions that, when executed, cause the processor to preform a test procedure to determine parameters for a stereo pair of images for a left eye and a right eye of a user performing surgery, wherein the test procedure comprises the user performing the surgery; adjust and correlate a plurality of parameters associated with a camera system based on feedback from the test procedure, wherein the plurality of parameters comprise any of resolution, magnification, disparity, brightness, contrast, color rendering index, and focus; and store the determined parameters as default values for the user.

Figure 12:
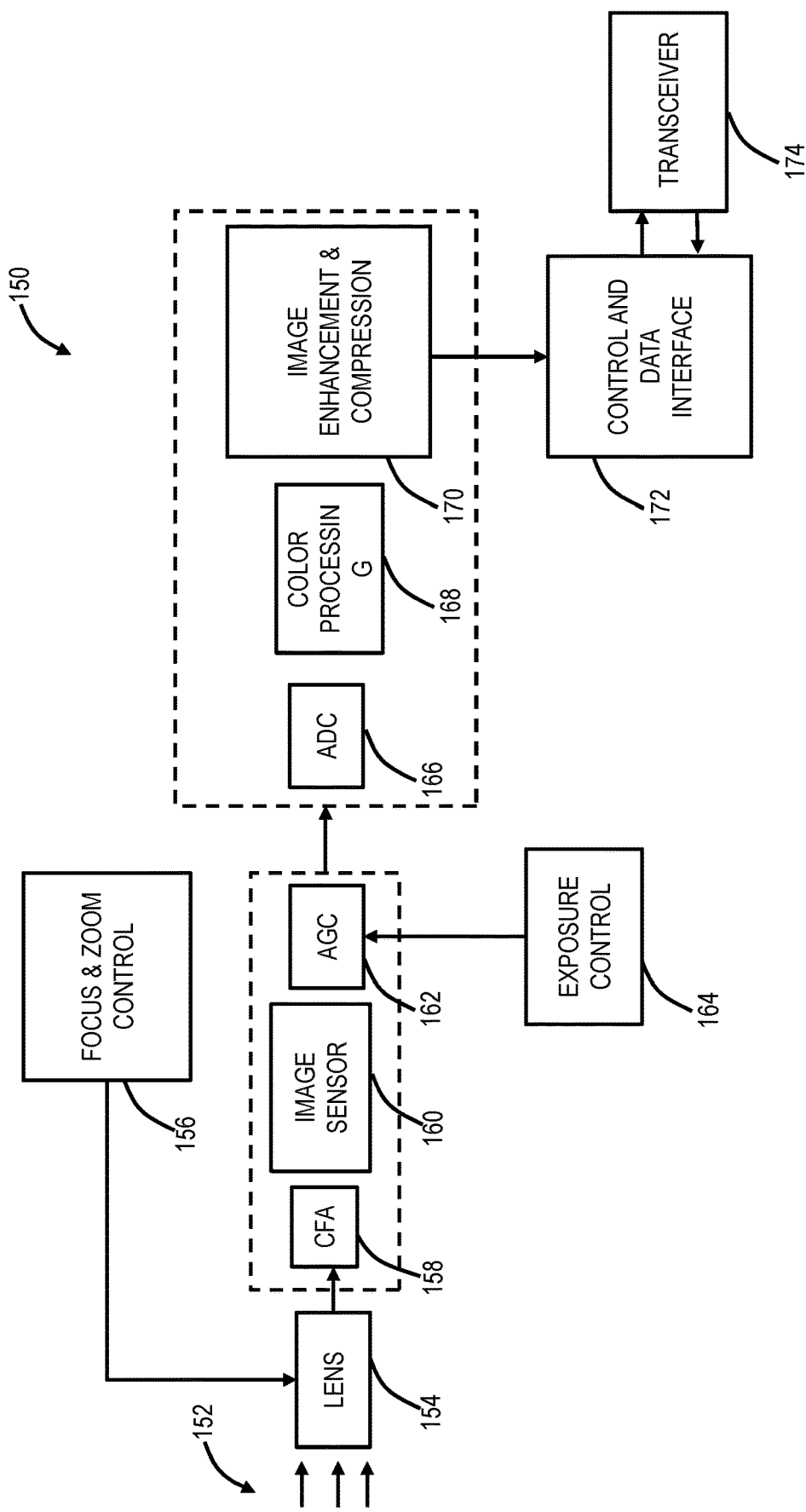
FIG. 12 describes a block diagram of an exemplary image acquisition system.

Referring to FIG. 12, in an exemplary embodiment, a block diagram illustrates an exemplary image acquisition system 150, such as for the and the image processing system 105. Imagery 152 is received at a lens 154, which is controlled by focus and zoom control 156. The lens 154 provides the imagery 152 to a Color Filter Array (CFA) 158, image sensor 160, and Automatic Gain Control (AGC) 162 which is controlled by exposure control 164. An output is provided to an Analog-Digital Converter (ADC) 166 where it is provided to a color processing module 168, an image enhancement and compression module 170, and a control and data interface 172 where it is interfaced via a transceiver 174.

Figure 13:
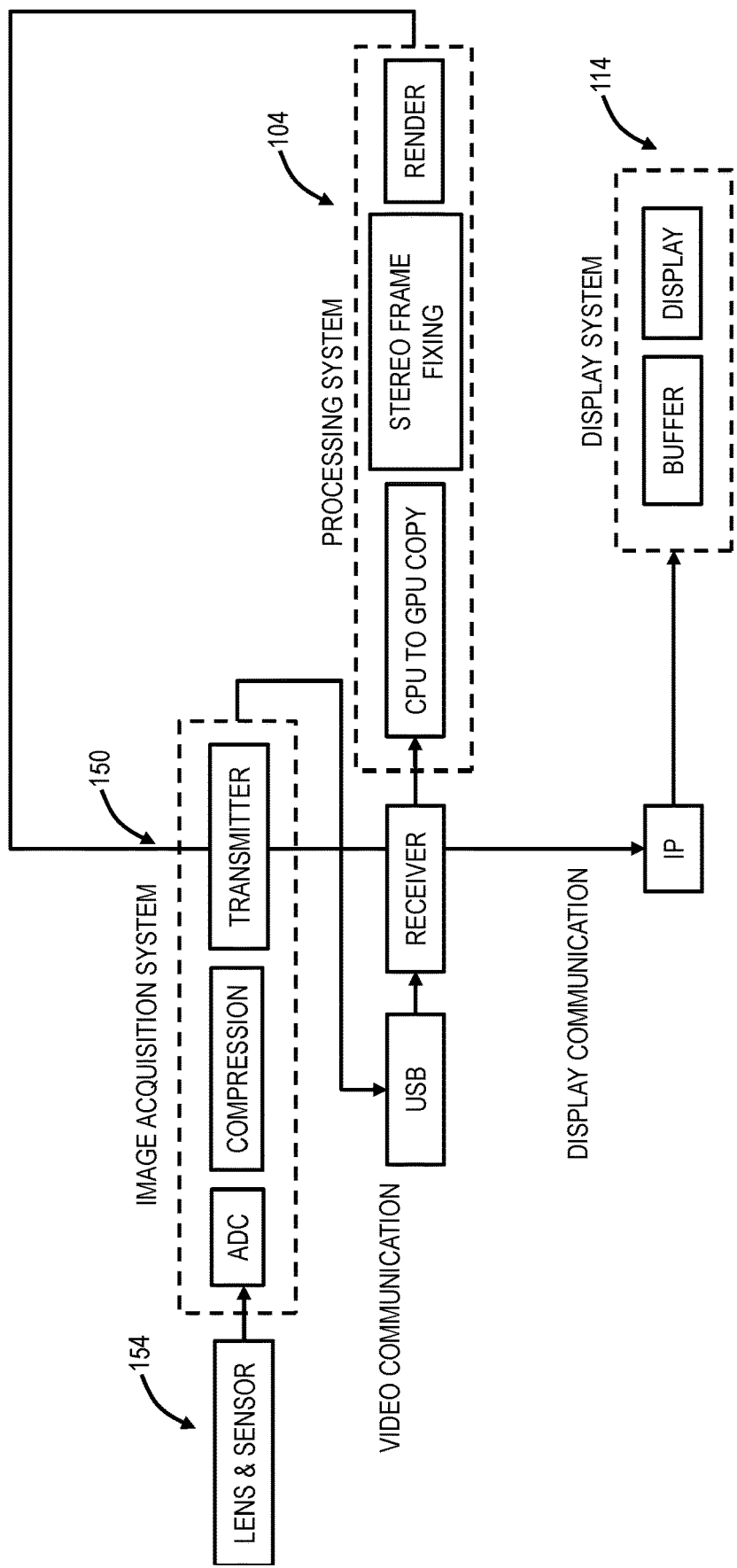
FIG. 13 describes a block diagram of various commonly occurring components of the delay in the digital stereo microscope system.

Referring to FIG. 13, in an exemplary embodiment, a block diagram illustrates various commonly occurring components of the delay in the digital stereo microscope system 100. A camera produces a frame by reading the sensor matrix in a short interval. Reading the sensor matrix converts the voltage level attained due to exposure to light through an analog to digital conversion, if the conversion takes about 50 ns, then for a 1920×1080 sensor matrix, it would require $1920 \times 50 \times 1080/10^6 \sim 105$ milliseconds. The operation of reading can be continuous after the desired exposure time. Suppose one were to produce, 30 Frames Per Second (FPS), which indicates that the same column of the sensor will be read again in 33.33 milliseconds. The number of analog-to-digital conversion pipelines needed will be roughly 3 making the camera compact. However, the frames incur a delay of 105 milliseconds for the first frame from capture until the frame is formed assuming that the framing time is negligible. By having ADCs per column, the framing time can be reduced to a fraction of a millisecond. However, it will increase the circuit complexity. From the specification of the camera (1920×1080 @ 30 FPS), it is not possible to know the level of the ADC integration. Hence the delay of the frames will not be noticed from this model.

Figure 14:
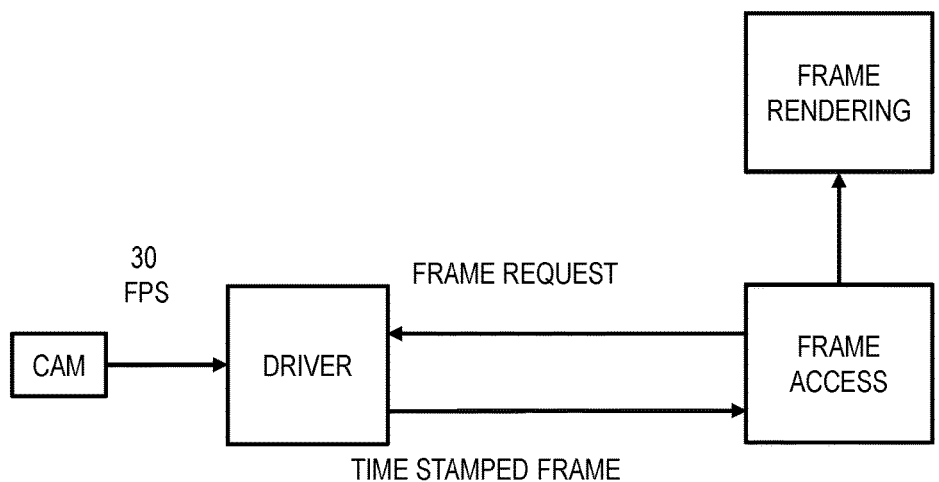
FIG. 14 describes synchronous requests in the video processing system.
Figure 17:
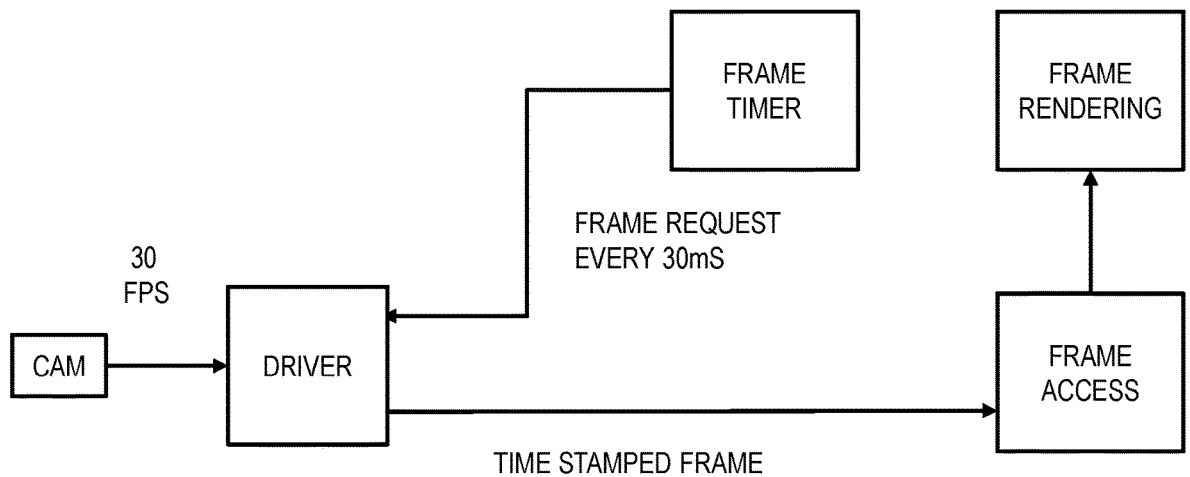
FIG. 17 describes asynchronous requests in the video processing system.
Figure 15:
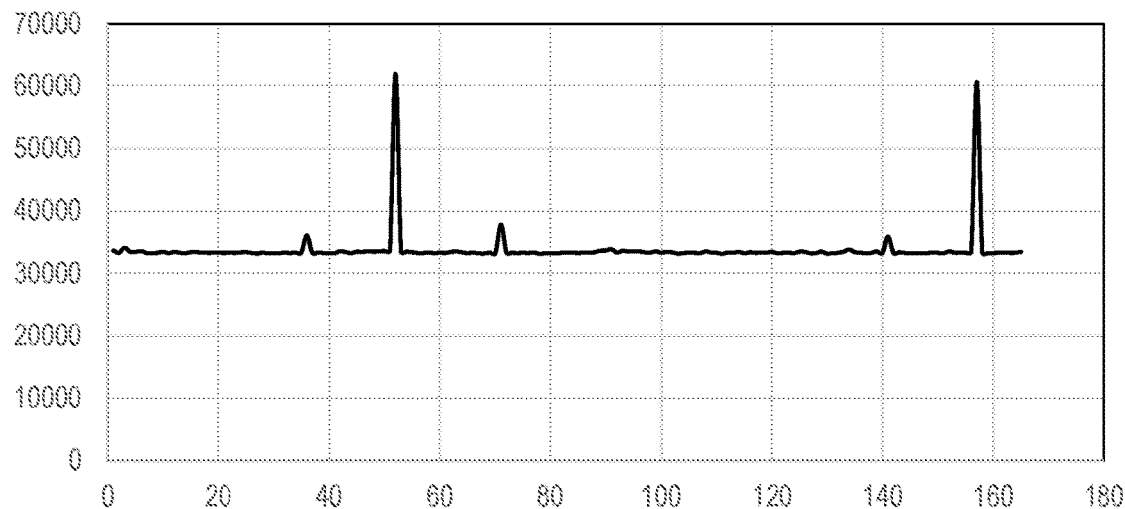
FIGS. 15 and 16 describe associated exemplary for the synchronous requests in the video processing system of FIG. 14.
Figure 16:
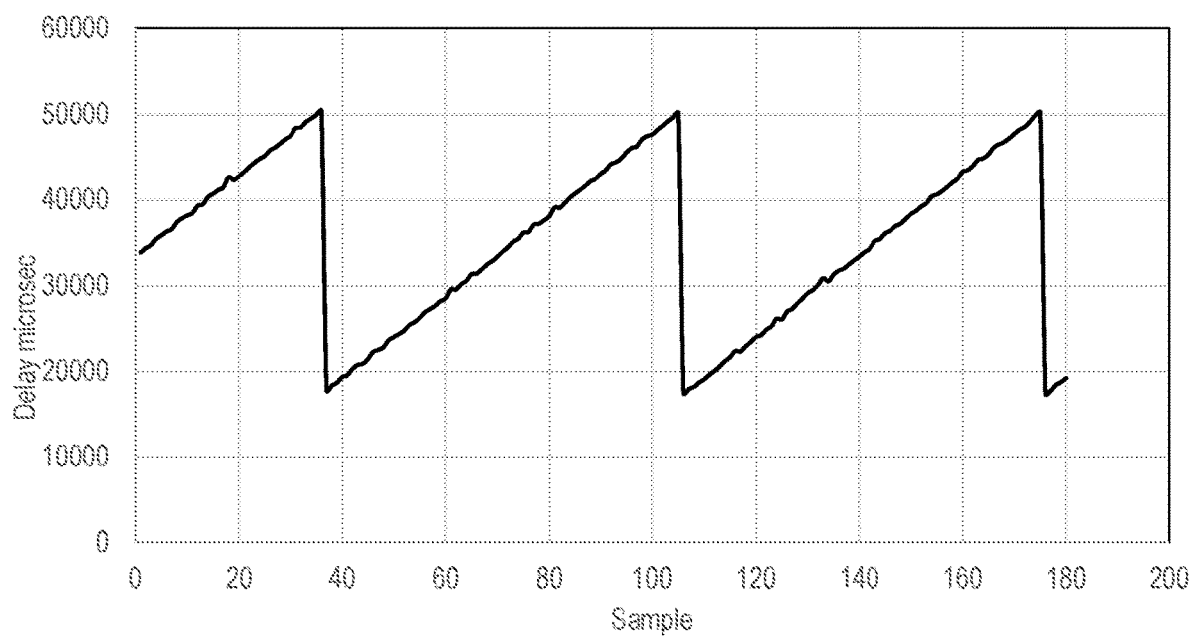
Figure 18:
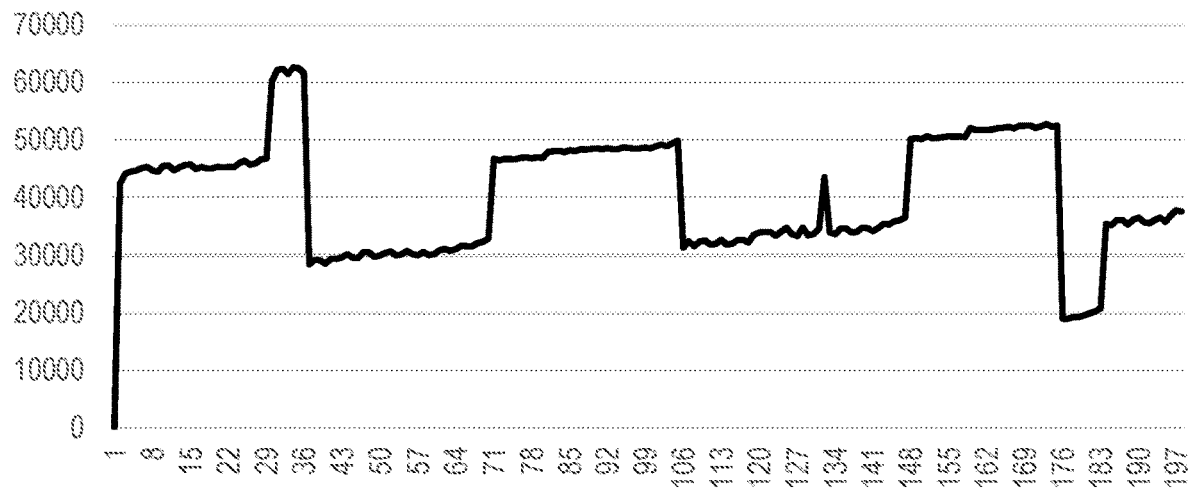
FIGS. 18 and 19 describe associated exemplary for the asynchronous requests in the video processing system of FIG. 17.
Figure 19:
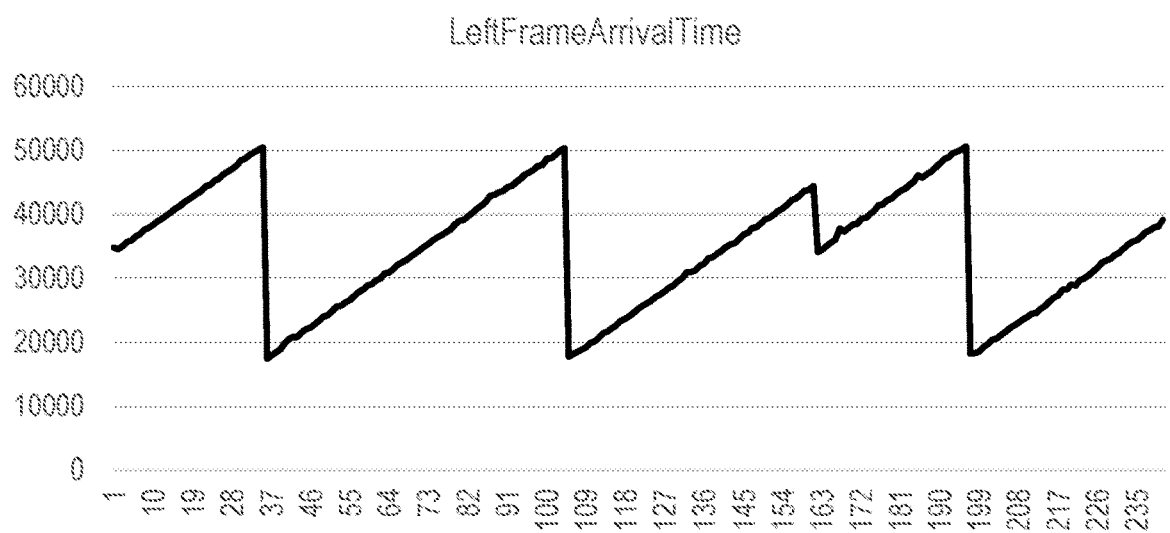

The quantum and type of delay is a combination of the delay elements shown in FIG. 13. The communication link delays vary with the type of link used. Accordingly, various configurations of the digital stereo microscope system 100 shown in FIGS. 6-10 have different amount of delays, as well as other types of configurations of the system 100. FIG. 14 illustrates synchronous requests in the video processing system 104 with associated exemplary delays illustrates in FIGS. 15 and 16. FIG. 17 illustrates asynchronous requests in the video processing system 104 with associated exemplary delays illustrates in FIGS. 18 and 19. A digital stereo microscope system 100 must compensate for these delays to provide a realistic feel of the workspace the surgeon is operating.

The digital stereo microscope system 100 is designed such that there is always a bounded delay path to the video frames which may include bypassing the processing done at the video processing system 104. For this purpose, the cameras in the camera system 102 are arranged such a way that the associated captured image pairs from the imaging processing system 105 are stereoscopic pairs with minimal distortion.

In addition, the frames may be uncompressed so that the time required for compressing and decompressing the frames is avoided. However, this could increase the frame transmission and reception times. For example, if the compression reduces the frame by a factor of 4, and assuming that the effective bandwidth of a USB 3.0 link is 1 Gbps, the transmission and reception of a full HD video in 8 bit color (YUY2 converted) will be 1920×1080×8/1000 microseconds which is roughly 16.5 milliseconds. By having 1/4th the payload, the transmit time will be 4.1 milliseconds. The difference of 12.4 milliseconds at transmit and an equal amount at reception may be used to perform compression and decompression if the time for compression and decompression together is more than the time for transmittal and reception.

Personalization of DSM

Figure 20:
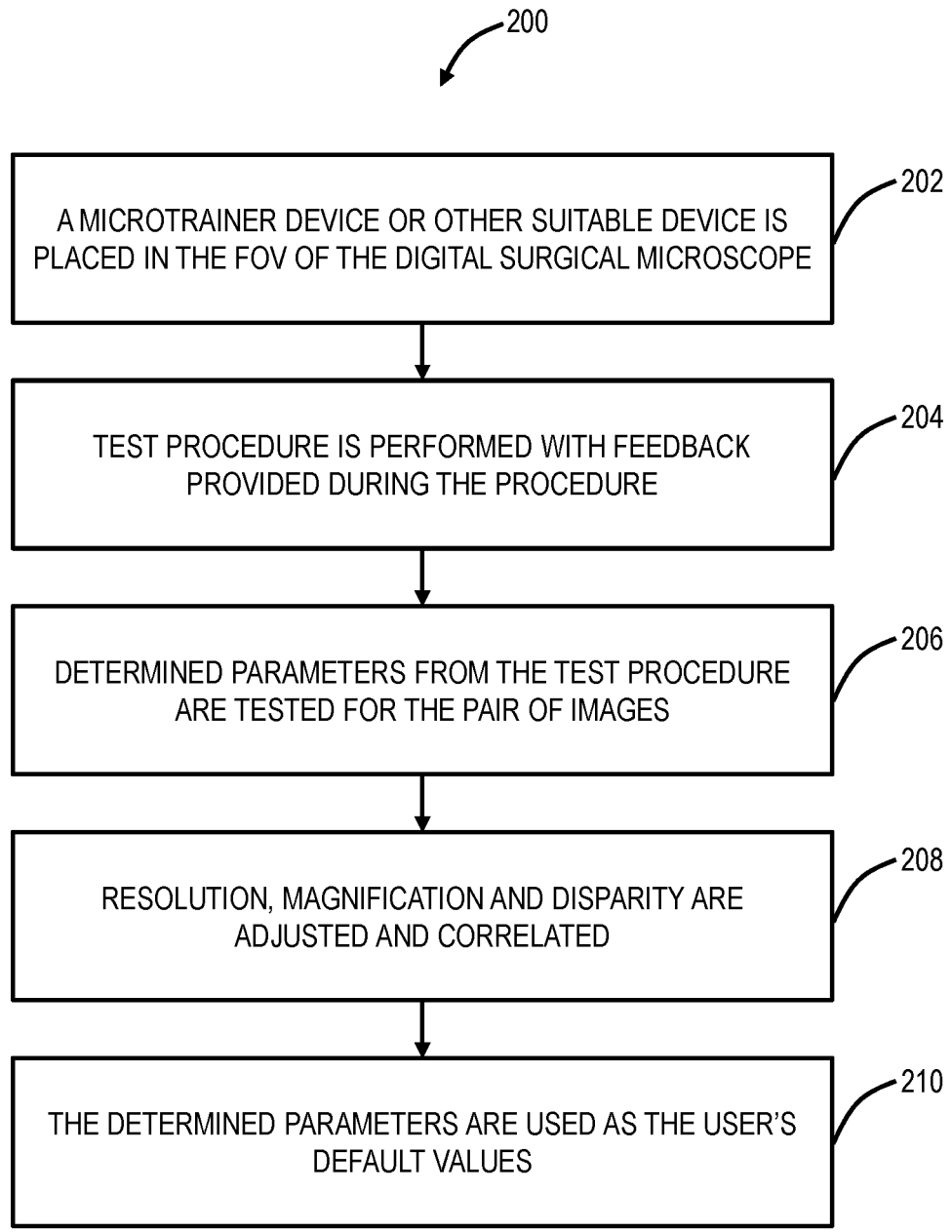
FIG. 20 is a flow chart of a personalization method for the digital stereo microscope system.

Referring to FIG. 20, in an exemplary embodiment, a flow chart illustrates a personalization method 200 for the digital stereo microscope system 100. The purpose of the personalization method 200 is to determine the tolerable limits on delay, delay variation, magnification, and resolution for any given user of the digital stereo microscope system 100. The personalization method 200 includes a microtrainer device or other suitable device is placed in the FoV of the digital surgical microscope 100 (step 202), a test procedure is performed with feedback provided during the procedure (step 204), determined parameters from the test procedure are tested for the pair of images (step 206), resolution, magnification and disparity are adjusted and correlated (step 208), and the determined parameters are used as the user's default values (step 210).

In the step 202, a microtrainer device or other suitable device is placed in the FoV of the digital surgical microscope. For example, a microtrainer device is described in Rappel et al, U.S. patent application Ser. No. 13/667,066, filed Nov. 2, 2012, and entitled "APPARATUS, METHOD AND SYSTEM FOR MICROSURGICAL SUTURE TRAINING," the contents of which are incorporated by reference herein. For example, the microtrainer device can be mounted with a pre-sutured latex strip and the magnification, resolution and focus are adjusted so that the suture is visible clearly. Once the magnification, resolution and focus are resolved for the surgeon, these can be recorded as the initial values. The limits on the resolution and magnification are recorded. This is performed in a monocular view and all the cameras are tested in the same mode.

In the step 204, a latex strip or the like of standard dimension can be mounted, and using a needle (e.g., 9-0 or 10-0 needle), suturing of the severed ends of the latex strip can be attempted. During this procedure, the user is asked to push the foot pedal if the digital stereo microscope system 100 is producing video which lacks clarity or hand-eye coordination. The digital stereo microscope system 100 internally varies the frame delay and adjust the resolution accordingly. In one attempt, the digital stereo microscope system 100 increases the delay and increases the resolution while, in another attempt after a push pedal, the digital stereo microscope system 100 decreases the delay and decreases the resolution. After a few pushes of the foot pedal, the changes in resolution and delay that the surgeon can accommodate is determined.

In the step 206, in a third phase, the determined parameters are tested for the pair of images, created by the camera system 102. In order to test whether both selected cameras are producing identical delay, a counter that steps by the maximum tolerable delay is produced. For example, if the tolerable delay was 120 milliseconds, then a counter that increments every 120 milliseconds is displayed in the FoV of the cameras. The image is captured by both the left and right cameras and displayed as stereo pairs. If the same clear image is seen by the viewer, then the delay is agreeable across the cameras. The exposure time of the camera is controlled or the start capture time of the camera is controlled if the images becomes blurry due to different counter values being read by both the cameras.

In the step 208, in a fourth phase, the resolution, magnification and disparity are adjusted and correlated. For adjusting the disparity, a pair of images of an actual blood vessel captured by the same cameras of the digital stereo microscope system 100 and stored in the digital stereo microscope system 100 are displayed. The images are captured at various resolutions and magnifications. The subset of image pairs of resolution and magnification matching the resolution and magnification identified by the surgeon in the step 202 is selected and displayed. Each image pair the disparity is adjusted so that the user views image in 3D with comfort. Vertical disparity, if any, is corrected. A range of horizontal disparity for the user is recorded for each image pair having its own magnification and resolution.

In the step 210, the determined parameters are used as the surgeon's default values. The digital stereo microscope system 100 adopts the resolution, magnification, disparity and delay to determine whether the digital stereo microscope system 100 can operate under these conditions. If not, a different set of cameras can be selected based on the parameters and the tests are repeated until the determined parameters matches the digital stereo microscope system 100 and the user.

There are many advantages of the digital stereo microscope system 100 and the personalization method 200. Like a surgical Loupe, the camera, the view and perception of depth and the real-time nature are personalized so that the strain on the individual surgeon is minimized. However, unlike the surgical Loupe, the surgeon does not need to be bothered by the magnified view outside of the work space. Surgeon wears only a shutter glass to aid stereopsis.

The digital stereo microscope system 100 can be produced in the smallest form factor since the transformations to be done on the image can be predetermined. It is possible to use the device connected to a remote processing system which can perform more complex analysis to compute the transformation matrices needed in the rendering of the stereo images.

A same graphics pipeline can be programmed to cater for a number of users, potentially increasing the ability to share the digital stereo microscope system 100.

The digital stereo microscope system 100 can be used to view the same scene by different users using their devices and common captured images. Each user sees the depth, resolution and delay in his/her convenient configuration.

The digital stereo microscope system 100 can be portable, it can be used in places where there is not enough facility to install and operate an optical stereo microscope. Since the digital stereo microscope system 100 is programmable, it is available for building various applications.

It will be appreciated that some exemplary embodiments described herein may include one or more generic or specialized processors ("one or more processors") such as microprocessors, digital signal processors, customized processors, and field programmable gate arrays (FPGAs) and unique stored program instructions (including both software and firmware) that control the one or more processors to implement, in conjunction with certain non-processor circuits, some, most, or all of the functions of the methods and/or systems described herein. Alternatively, some or all functions may be implemented by a state machine that has no stored program instructions, or in one or more application specific integrated circuits (ASICs), in which each function or some combinations of certain of the functions are implemented as custom logic. Of course, a combination of the aforementioned approaches may be used. Moreover, some exemplary embodiments may be implemented as a non-transitory computer-readable storage medium having computer readable code stored thereon for programming a computer, server, appliance, device, etc. each of which may include a processor to perform methods as described and claimed herein. Examples of such computer-readable storage mediums include, but are not limited to, a hard disk, an optical storage device, a magnetic storage device, a ROM (Read Only Memory), a PROM (Programmable Read Only Memory), an EPROM (Erasable Programmable Read Only Memory), an EEPROM (Electrically Erasable Programmable Read Only Memory), Flash memory, and the like. When stored in the non-transitory computer readable medium, software can include instructions executable by a processor that, in response to such execution, cause a processor or any other circuitry to perform a set of operations, steps, methods, processes, algorithms, etc.

Although the present disclosure has been illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the present disclosure, are contemplated thereby, and are intended to be covered by the following claims.

What is claimed is:

1. A personalized digital microscope system for use in microsurgery, comprising:
   a camera system comprising an array of camera pairs, each camera pair configured to produce a stereo pair of images captured in real-time;
   an image processing system communicatively coupled to the camera system and configured to extract the stereo pair of images, captured by a camera pair, synchronized in time with each other and to combine the stereo pair of images with encoded images of differences between the stereo pair of images; and
   a video processing system communicatively coupled to the image processing system and configured to create a stream from the encoded images of the camera pair by processing the encoded images based on parameters to personalize the processing by the video processing system for the user,
   wherein the parameters are determined based on a test procedure performed by the user,
   wherein the parameters for the user are stored for use by the video processing system during the processing of the encoded images and for use by the image processing system to select the camera pair from the array of camera pairs based thereon, and
   wherein the parameters obtained from the test procedure relate to at least one of the stereo acuity of the user, ocular muscle abilities of the user, interpupillary distance of the user, and a dominant eye of the user.

2. The personalized digital microscope system of claim 1, further comprising:
   a display monitor configured to receive the stream for display, wherein the user wears a programmable shutter glass to view the display monitor.

3. The personalized digital microscope system of claim 1, further comprising:
   a second display monitor configured to receive a second stream for display for a second user, wherein the second stream is based on parameters for the second user, and wherein the parameters for the second user are stored for use by the video processing system during the processing of the encoded images for the second user and for use by the image processing system to select a second camera pair from the array of camera pairs based thereon such that the second stream for the second user is different than the stream for the user.

4. The personalized digital microscope system of claim 1, wherein a parameter relating to the stereo acuity of the user is obtained during the test procedure by matching the interpupillary distance of the user to stereo disparity on a display used during the test procedure.

5. The personalized digital microscope system of claim 1, wherein the microsurgery comprises a micro-suture and the personalization is performed by initially setting magnification, a plurality of parameters of the digital stereo microscope system so that the suture is visible, wherein initial settings are recorded, and operation of one or more test procedures.

6. The personalized digital microscope system of claim 1, wherein the parameters include a parameter based on a type of microsurgery and associated biological tissues involved, tools, and materials.

7. The personalized digital microscope system of claim 1, further comprising:
   an interface configured for receiving inputs from the user for manually adjusting the stream.

8. A personalization method for a digital stereo microscope system comprising a camera system configured to produce a stereo pair of images, for a left eye and a right eye of a user, the personalization method comprising:
   performing a test procedure by the user with the digital stereo microscope system and providing feedback during the test procedure;
   testing determined parameters from the test procedure for the stereo pair of images;
   adjusting and correlating resolution, magnification, and disparity from the testing of the stereo pair of images;
   storing the determined parameters from the adjusting and correlating as default values for the user; and
   using the determined parameters to process images on a digital microscope system, the digital microscope system comprising:

a camera system comprising an array of camera pairs, each camera pair configured to produce a stereo pair of images captured in real-time;

an image processing system communicatively coupled to the camera system and configured to extract the stereo pair of images, captured by a camera pair, synchronized in time with each other and to combine the stereo pair of images with encoded images of differences between the stereo pair of images; and a video processing system communicatively coupled to the image processing system and configured to create a stream from the encoded images of the camera pair by processing the encoded images based on the determined parameters to personalize the processing by the video processing system for the user, wherein the determined parameters for the user are stored for use by the video processing system during the processing of the encoded images and for use by the image processing system to select the camera pair from the array of camera pairs based thereon, and wherein the determined parameters relate to at least one of the stereo acuity of the user, ocular muscle abilities of the user, interpupillary distance of the user, and a dominant eye of the user.

9. The personalization method of claim 8, wherein the test procedure comprises a micro-suture and initially setting magnification, resolution and focus of the digital stereo microscope system so that the suture is visible, wherein initial settings are recorded.

10. The personalization method of claim 8, wherein the test procedure is performed in a monocular view of the camera system.

11. The personalization method of claim 8, wherein the feedback is an indication from the user that the digital stereo microscope system is producing video which lacks clarity or hand-eye coordination, wherein the digital stereo microscope system is configured to vary frame delay and adjust resolution based on the feedback.

12. The personalization method of claim 8, wherein the adjusting and correlating utilizes an actual blood vessel being sutured by the camera system, images of the actual blood vessel are displayed and adjusted per the user.

13. The personalization method of claim 8, further comprising:

adjusting the stereo pair of images based on the user's dominant eye.

* * * * *